(12) United States Patent
Kondoh et al.

(10) Patent No.: US 8,487,087 B2
(45) Date of Patent: Jul. 16, 2013

(54) MODEL ANIMAL IN WHICH STATE OF DISEASE CONDITION IS OBSERVABLE IN REAL TIME, GENE CONSTRUCT FOR ACHIEVING THE SAME AND USE OF THE SAME

(75) Inventors: Shinae Kondoh, Kyoto (JP); Hiroshi Harada, Kyoto (JP); Masahiro Hiraoka, Kyoto (JP); Shu-ichi Yamada, Kyoto (JP)

(73) Assignee: Oriental Yeast Co., Ltd., Tokyo (JP)

( * ) Notice: Subject to any disclaimer, the term of this patent is extended or adjusted under 35 U.S.C. 154(b) by 1007 days.

(21) Appl. No.: 11/908,202

(22) PCT Filed: Mar. 10, 2006

(86) PCT No.: PCT/JP2006/304701
§ 371 (c)(1),
(2), (4) Date: Apr. 12, 2010

(87) PCT Pub. No.: WO2006/095846
PCT Pub. Date: Sep. 14, 2006

(65) Prior Publication Data
US 2010/0275283 A1 Oct. 28, 2010

(30) Foreign Application Priority Data

Mar. 11, 2005 (JP) .................................. 2005-69013

(51) Int. Cl.
*C07H 21/04* (2006.01)
*C12N 5/00* (2006.01)
*C12Q 1/68* (2006.01)

(52) U.S. Cl.
USPC ........................... 536/23.2; 435/325; 435/6.1

(58) Field of Classification Search
USPC ..................................... 536/23.2; 435/325, 6
See application file for complete search history.

(56) References Cited

U.S. PATENT DOCUMENTS 5,834,306 A 11/1998 Webster
6,787,326 B1 * 9/2004 Ratcliffe et al. ................ 435/14

FOREIGN PATENT DOCUMENTS

| WO | WO-02/26192 | 4/2002 |
| WO | WO-02/099104 | 12/2002 |
| WO | WO-2004-031357 | 4/2004 |
| WO | WO-2004/042361 | 5/2004 |

OTHER PUBLICATIONS

Radiation Biology Research Communication, Dec. 27, 2002, pp. 376-392, vol. 37, No. 4, ,s, Kondo et al.
Bio Clinica, Jan. 10, 2005, pp. 53-58, vol. 20, No. 1, Kondo et al.
Koshikawa et al, "Hypoxia-regulated expression of attenuated diphtheria toxin A fused with a hypoxia-inducible factor-lalpha oxygen-dependent degradation domain preferentially induces apoptosis of hypoxic cells in solid tumor", Dec. 2005, pp. 11622-11630, vol. 65, Cancer Research.
Salnikow et al, "Depletion of intracellular ascorbate by the carcinogenic metals nickel and cobalt results in the induction of hypoxic stress", Sep. 24, 2004, pp. 40337-40344, vol. 279, No. 39, The Journal of Biological Chemistry.
Harada et al., "Antitumor effect of TAT-oxygen-dependent specifically stabilized and activated in hypoxic tumor cells", Apr. 1, 2002, pp. 2013-2018, vo. 62, No. 7, Cancer Research.

* cited by examiner

*Primary Examiner* — Marcia S Noble
(74) *Attorney, Agent, or Firm* — B. Aaron Schulman, Esq.; Stites & Harbison, PLLC

(57) ABSTRACT

Provided is a technique for observing in real time the state of a disease condition in a tissue of an animal or the state of a functionally adverse condition which is a prelude to the disease condition without injuring the animal. This can be achieved by the use of a gene construct having a reporter gene integrated under the control of a hypoxia responsible promoter an ODD domain (oxygen dependent degradation domain) integrated upstream to the reporter gene.

8 Claims, 12 Drawing Sheets

MODEL ANIMAL IN WHICH STATE OF DISEASE CONDITION IS OBSERVABLE IN REAL TIME, GENE CONSTRUCT FOR ACHIEVING THE SAME AND USE OF THE SAME

TECHNICAL FIELD

The present invention relates to a gene construct, and more particularly, to a gene construct that allows observing in real time changes in the disease condition of an animal.

Also, the present invention relates to an expression vector comprising the gene construct, mammalian cells, a transgenic nonhuman mammal, use of a nonhuman mammal for observing in real time changes in the disease condition of an animal, and a method for screening drugs, genes and proteins.

BACKGROUND ART

Oxygen tension distribution is not homogeneous within a solid tumor, inside which tumor cells are exposed to various oxygen environments. This arises from limitations in the distance by which oxygen molecules diffuse from blood vessels to the tumor tissue.

As is known, expression of target genes such as therapeutic genes, reporter genes and the like can be induced in a hypoxic environment by using hypoxia-responsive enhancers such as HREs or the like.

However, such gene expression systems were problematic in that the genes are expressed also, although slightly, in aerobic conditions. Moreover, response in real time to the oxygen environment in which the cell is placed was difficult owing to the stability of reporter genes. Specifically, there were no reporters that, although capable of sensing a hypoxic stimulus in an existing system, did sense thereafter an aerobic stimulus (re-oxygenation) in a short lapse of time, and hence it was not possible to reflect in real time the oxygen environment in which the cells were placed. As is known, moreover, such hypoxia-responsive promoters are activated not only in a hypoxic environment, but also in some abnormal cells that result, directly or indirectly, from the hypoxic environment. In light of the possibility of sensing various disease conditions that result directly or indirectly from a hypoxic environment, therefore, there was a strong interest in the development of gene expression systems that should have high responsiveness to environments that are intimately involved in a disease condition.

Patent documents 1 and 2 disclose a combination of a reporter gene and a hypoxia inducible promoter (HRE), but recite nothing concerning ODD.

Patent document 3 discloses a combination of a reporter gene and NLS-ODD, but recites nothing concerning a hypoxia inducible promoter (HRE).

Patent document 1: Japanese Translation of PCT Application H11-506302

Patent document 2: Japanese Translation of PCT Application 2004-509635

Patent document 3: WO2002/099104

DISCLOSURE OF THE INVENTION

Problems to be Solved by the Invention

An object of the present invention is to provide a technology for observing, in particular observing in real time, a disease condition in animal tissue, without hurting the animal.

Means for Solving the Problems

The present invention relates to a below-described gene construct, an expression vector comprising the gene construct, mammalian cells, a transgenic nonhuman mammal, use of a nonhuman mammal for observing in real time changes in the disease condition of an animal, and a method for screening candidate compounds or genes.

1. A gene construct which has a reporter gene integrated under the control of a hypoxia responsive promoter, and in which an ODD domain (oxygen dependent degradation domain) is fused in-frame (with corresponding codon) to the reporter gene.

2. The gene construct according to item 1, wherein the hypoxia-responsive promoter has a HIF-1 binding domain (HRE: hypoxia responsive element).

3. The gene construct according to item 1, wherein the hypoxia-responsive promoter has a minimal promoter (mp).

4. The gene construct according to any of items 1 to 3, wherein the reporter gene is a luciferase gene.

5. The gene construct according to any of items 1 to 4, further comprising a nuclear localizing signal (NLS).

6. The gene construct according to item 5, having a (HIF-1 binding domain)-(mp)-(NLS)—(ODD domain)-(reporter gene) structure.

7. A transformant obtained by transfecting a host cell with the gene construct according to any of items 1 to 6.

8. A transgenic nonhuman mammal obtained by introducing the gene construct according to any one of items 1 to 6 in the nonhuman mammal.

9. The transgenic nonhuman mammal according to item 8, wherein the nonhuman mammal is a mouse.

10. A transgenic nonhuman mammal obtained by crossing the transgenic nonhuman mammal according to item 8 or 9 with another nonhuman mammal having characteristics of an arbitrary disease condition, wherein the obtained transgenic nonhuman mammal allows analyzing in real time characteristics of the disease condition.

11. Use of the transgenic nonhuman mammal according to any of items 8 to 10, for monitoring a disease condition in real time.

12. A method for screening a candidate compound or a gene comprising the step of evaluating the candidate compound or the gene that influences expression or activity of a reporter gene in use of the gene construct according to any of items 1 to 6.

13. A method for evaluating or searching a candidate compound or a gene that influences a disease condition in use of the transgenic nonhuman mammal according to any of items 8 to 10.

Effects of the Invention

By being transfected into an animal cell, the gene construct of the present invention allows observing in real time not only oxygen concentration but also the progress from an initial stage of a disease up to a serious condition thereof, in accordance with the severity of the disease. FIG. 11, for instance, shows that $1.0 \times 10^4$ luciferase-expressing tumor cells can be detected. Since there are arguably at least some $4 \times 10^5$ tumor cells in a 1-mm tumor, i.e. the size of an actual tumor, the present invention allows therefore observing in vivo also tumors fairly smaller than 1 mm. Condition imaging of cancer can thus be reliably carried out in a transgenic nonhuman mammal obtained by transfecting the gene construct of the present invention, when the mammal develops a solid cancer. The effectiveness against cancer of a compound as a candidate anticancer agent can thus be assessed by administering the compound to a model animal of this cancer and observing the state of the cancer. The gene construct of the invention is thus useful in drug screening systems and/or as an evaluation system of physical therapy methods (for instance, surgery, radiotherapy, thermotherapy and the like).

The present invention can be ideally used in basic research on intra-tumor hypoxic environments that exhibit resistance to radiotherapy and/or anticancer agents, and for evaluating the pharmaceutical efficacy of drugs that affect the oxygen environment inside a tumor.

The present invention is useful, in particular for development of disease condition imaging and therapy of ischemic diseases, and disease condition imaging in model mice for naturally occurring cancer.

Other than cancer, the invention allows observing disease conditions relating to ischemic diseases such as angina pectoris, myocardial infarction, brain stroke and the like, diseases relating to diabetes complications such as peripheral circulation disorders, diabetic nephropathy, atherosclerosis and other ischemias such as decreased blood flow or artificial ischemia by blood vessel ligation or tissue constriction. The invention enables also, arguably, disease condition imaging of chronic inflammation models of gastric ulcers, duodenal ulcers and chronic inflammation of the respiratory system (which can be caused by involuntary inhalation of tobacco or exhaust gases of diesel or gasoline), as well as wide-ranging disease condition imaging of external injuries and of inflammatory conditions brought about by administration of inflammation-inducing substances to various organs and tissues.

Introducing the gene construct of the present invention allows evaluating disease condition changes in an organ or tissue without hurting the animal. Therefore, the present invention is extremely useful in the development of therapies that involve administration schedules of plural drugs.

Figure 1:
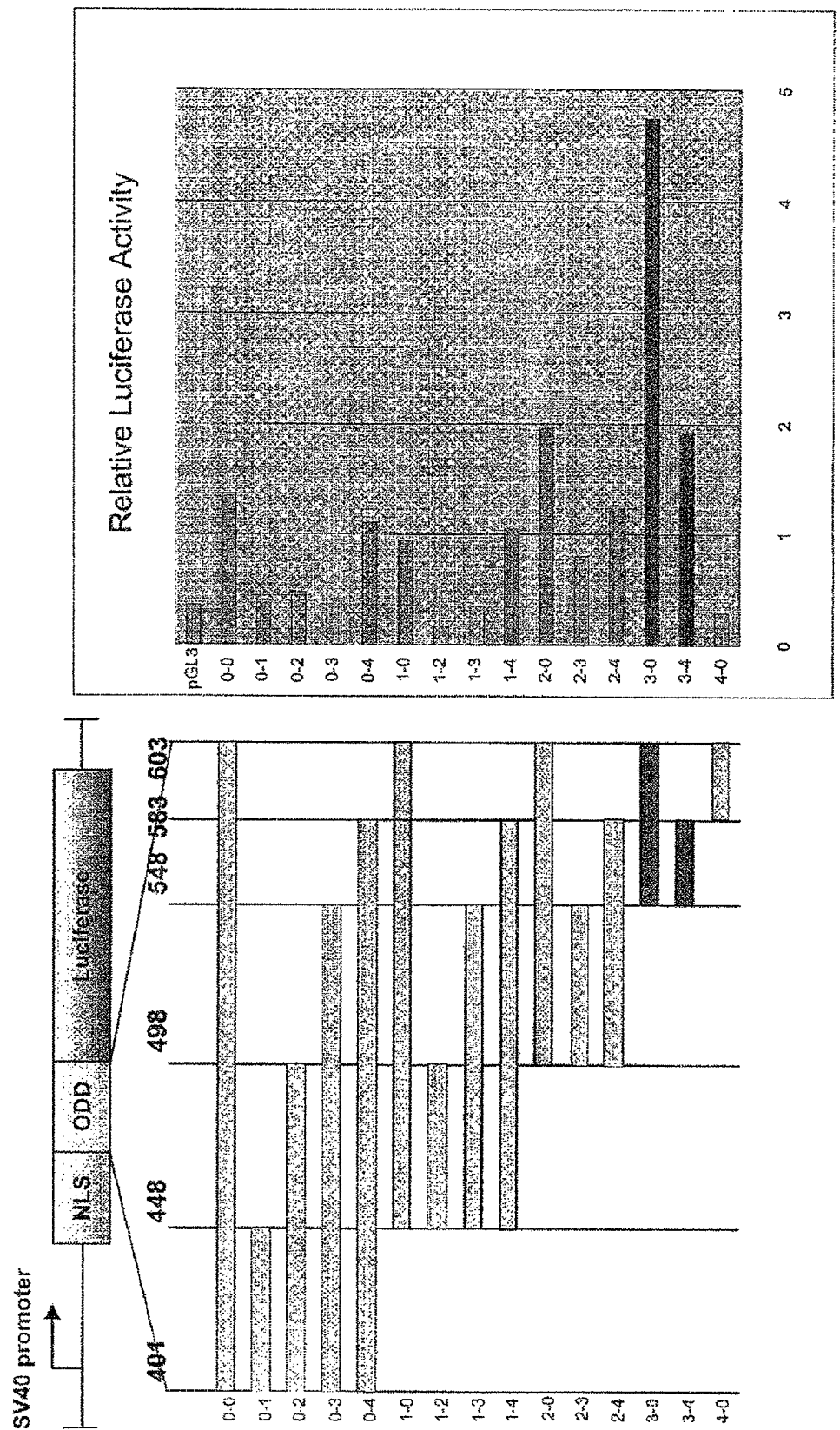
FIG. 1 Identification of Necessary Regions for Enzyme-Dependent Protein Stability Control The following experiment was carried out with a view to determining whether or not there was a difference in the efficiency of oxygen-dependent protein degradation as a result of ODD domain fusion.

A pGL3 promoter vector was BglII digested, then treated with T4 DNA polymerase, followed by treatment with DNA ligase, to construct a plasmid pGL3 Δ Bgl in which a mutation was introduced in the BglII recognition sequence of the pGL3 promoter vector.

A DNA fragment of NLS-ODD$_3$-0 (DNA fragment coding for NLS-ODD548-603) was amplified by PCR using a pCH/3-0 plasmid (Harada et al. 2002 Cancer Res.) as a template, and employing a NLS-Nco-sense primer; 5'-AAC CAT GGC GXX TAA GAA GAA GAG GAA G-3', and an ODD-Nco-anti primer; 5'-AAC CAT GGT CTG CTG GAA TAC TGT AAC TG-3'. After NcoI digestion, this DNA fragment was inserted at the NcoI position of the pGL3 Δ Bgl, to construct a pGL3 Δ Bgl/3-0 plasmid.

A plasmid pGL3 Δ Bgl Δ Nco/3-0, in which mutation is induced at the NcoI recognition site at the 5' terminus of the NLS-ODD-Luciferase fused gene that is expressed by pGL3 Δ Bgl/3-0, was constructed by site-directed mutagenesis. Hereinafter this plasmid will be denoted as pGL3/3-0.

Total RNA was extracted from a HeLa cell line derived from human cervical cancer using ISOGEN (Nippon gene). Using the extract as a template, cDNA of the human HIF-1α gene was obtained through reverse transcription reaction with AMV reverse transcriptase XL. Using now the cDNA as a template, PCR was carried out combining the —F and —R of the ten primers given in Table 1 (ODD-Bgl-F0, -F1, -F2, -F3, -F4, and ODD-Nco-R0, -R1, -R2, -R3, -R4), to obtain DNA fragments coding for systematically deleted ODD regions.

The DNA fragments were digested with BglII and NcoI, to yield BglII— and NcoI-digested termini at the 5' terminus and the 3' terminus, respectively, and to insert the DNA fragments into the plasmid vector manufactured through treatment of the pGL3/3-0 with BglII and NcoI. Through this gene recombination there were constructed plasmids for expressing the genes wherein various deleted DNA fragments of the ODD region (0-0, 0-1, 0-2, 0-3, 0-4, 1-0, 1-2, 1-3, 1-4, 2-0, 2-3, 2-4, 3-0, 3-4, 4-0), NLS, and luciferase are fused (pGL3/0-0, pGL3/0-1, pGL3/0-2, pGL3/0-3, pGL3/0-4, pGL3/1-0, pGL3/1-2, pGL3/1-3, pGL3/1-4, pGL3/2-0, pGL3/2-3, pGL3/2-4, pGL3/3-0, pGL3/3-4, pGL3/4-0 respectively).

HeLa cells were seeded on a 24-well culture dish (10000 cells/well). After 16 hours of incubation, the above plasmids (0.4 μg/well) were transfected using Polyfect Transfection Reagent (QIAGEN). A plasmid pRL/CMV (Promega) for constitutive expression of Renilla luciferase was also transfected simultaneously herein as an internal control (0.04 μg/well). The culture medium was replaced 24 hours after gene transfection, followed by further culture over 18 hours under aerobic or hypoxic conditions (oxygen concentration<0.02%). After suctioning off the culture medium, cell extracts were collected using 100 ml of Passive Lysis Buffer (Promega), and a dual luciferase assay was carried out in accordance with the accompanying instructions.

The results of the experiment show that oxygen concentration-dependent protein degradation efficiency is maximum when an ODD/3-0 domain sequence is fused.

Figure 2:
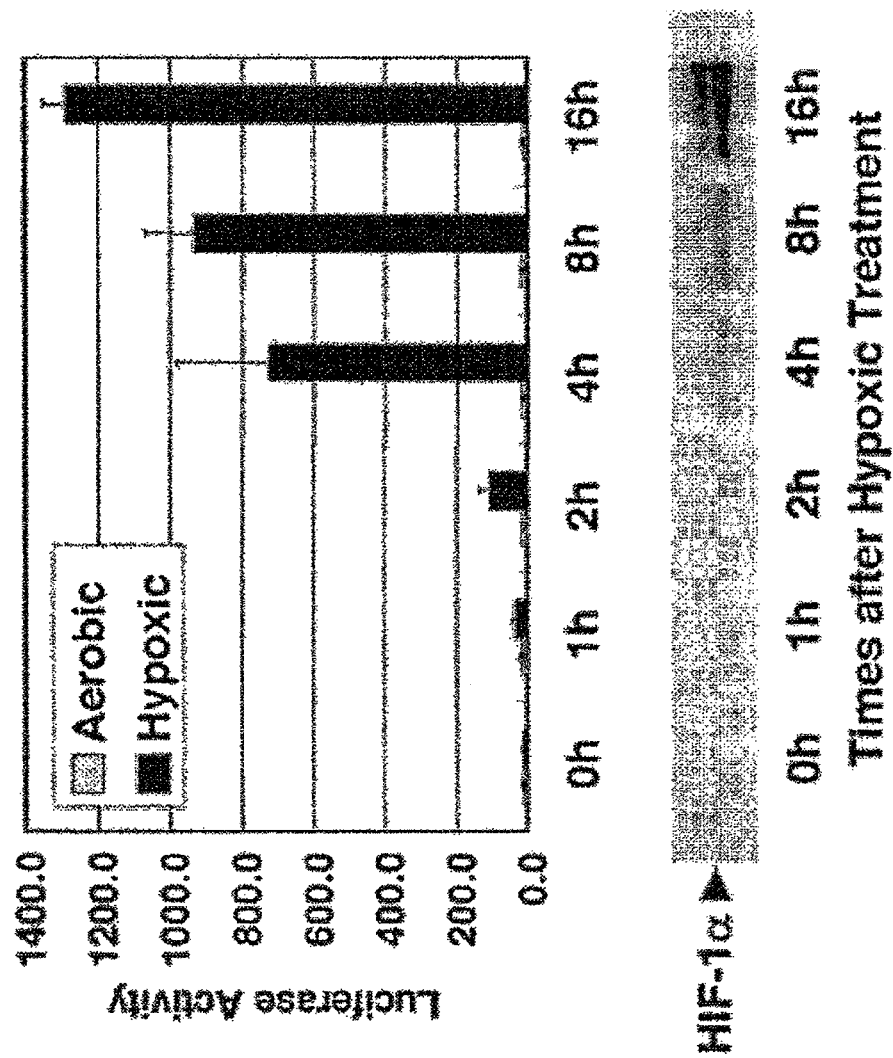

FIG. 2 Hypoxia-Responsive Control of 5HRE Promoter Activity

Figure 10:
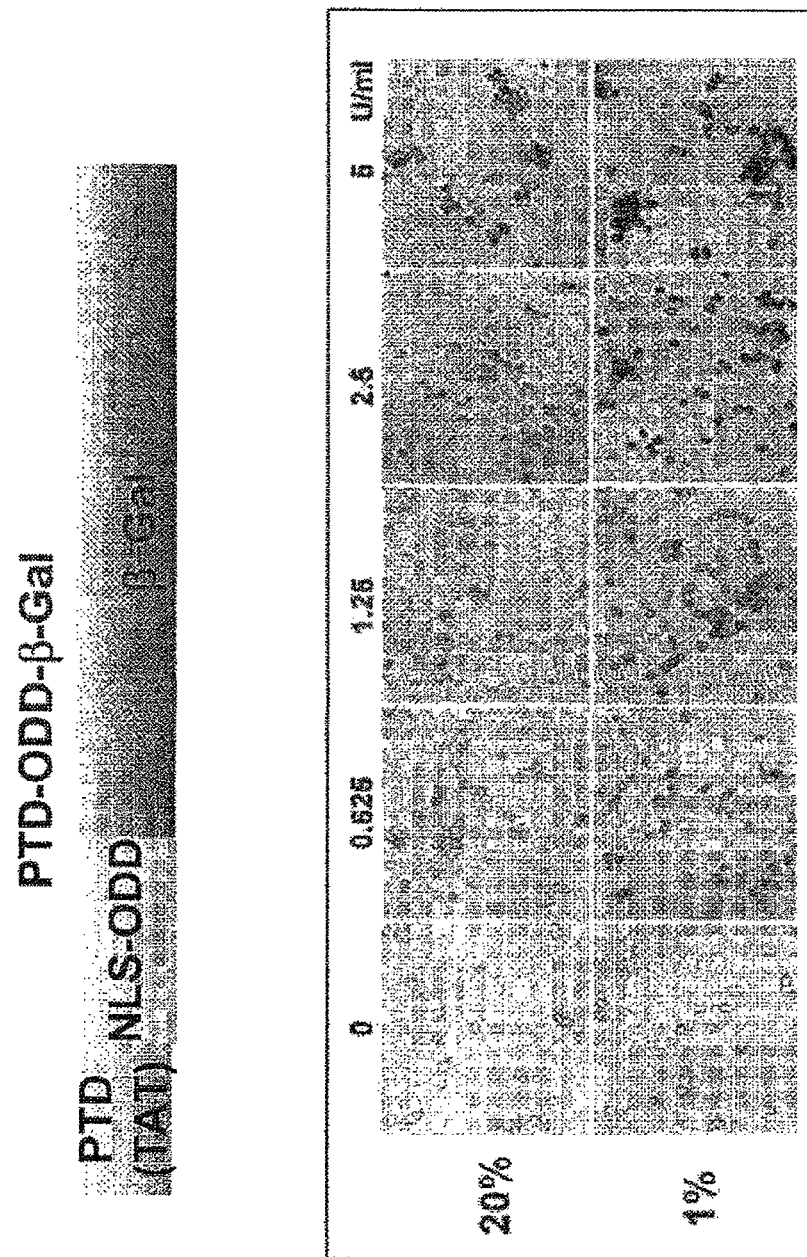

The limits of a degradation system can be sufficiently resolved through an ODD such as the one illustrated in FIG. 10, by using a hypoxia-specific promoter.

Figure 6:
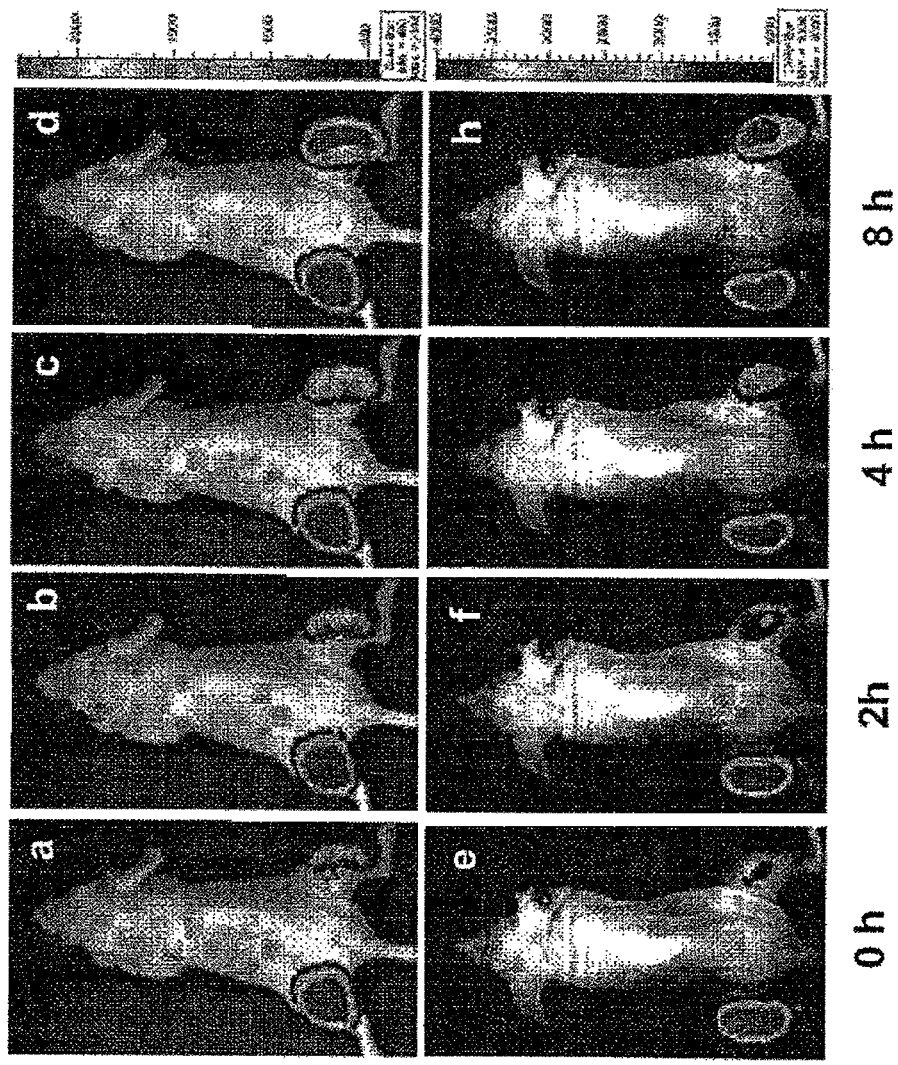

Cells transfected with 5HRE-Luc were cultured under aerobic (□) or hypoxic (■) conditions over the time indicated in the graph (top), and then the activity of the luciferase expressed in the cells was measured. The data are expressed as average and SD of the results of three experiments. The graph at the bottom gives the results of HIF-1α protein in the cells cultured hypoxically, as determined by western blot. Since the ODD-mediated degradation mechanism occurs similarly to the HIF-1α protein indicated by the western blot, expression of the reporter gene in the tissue in an aerobic condition can arguably be substantially suppressed by using 5HRE. Expression induction in tissues in a hypoxic state increases more than 100-fold as time wears on (through chronification), and hence imaging can be expected to strengthen also over time (FIG. 6 shows strengthening during actual in vivo imaging).

Figure 3:
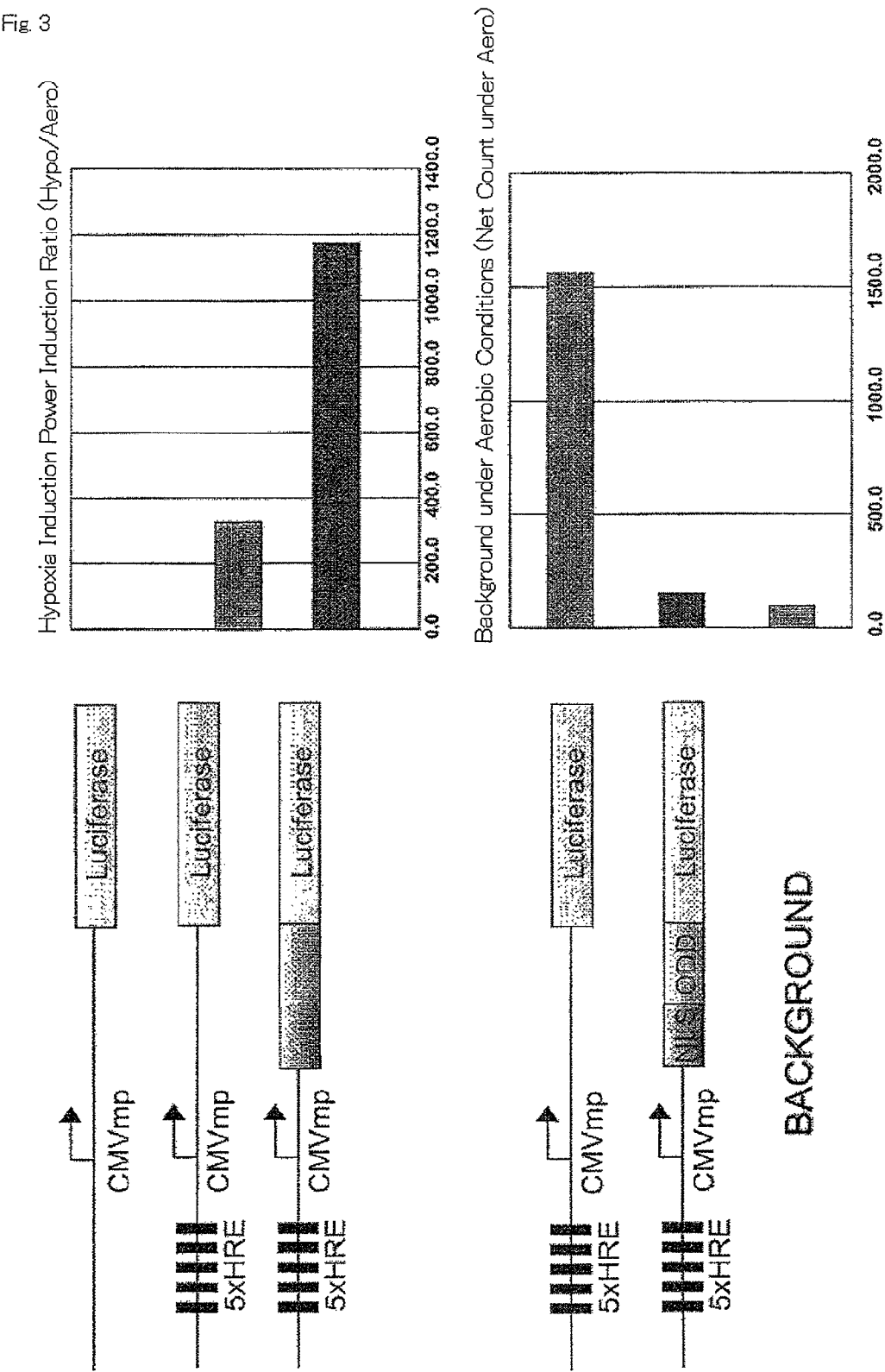

FIG. 3 Comparison with Existing Reporters (Hypoxic/Aerobic Ratio and Background for Luciferase Activity)

Expressions of the reporter gene when using 5HRE promoter and when using 5HRE combined with ODD were compared. In particular, the induction ratio (hypoxia/aerobic) (top graph) and aerobic expression (background) (bottom graph) were compared. The results indicate that the promoter where 5HRE is combined with ODD exhibited a smaller background and hence a dramatically enhanced induction ratio. FIG. 3 top: pGL3/5HRE-Luc or pGL3/5HREp-NLS-ODD-Luciferase (pGL3/5HRE-ODD-Luc) was transfected into HeLa cells together with pRL-CMV. A dual luciferase assay was carried out then after culture under hypoxic/aerobic conditions. The "ratio of firefly luciferase activity relative to Renilla luciferase activity" was calculated for hypoxic conditions and aerobic conditions, then the ratio for hypoxic conditions was calculated relative the ratio for aerobic conditions, to yield the induction ratio. FIG. 3 bottom: the activity (measured value) of firefly luciferase under aerobic conditions after the above treatment was plotted in a graph. A luciferase assay was performed using Passive Lysis Buffer instead of a cell extract, to measure Background.

Figure 4:
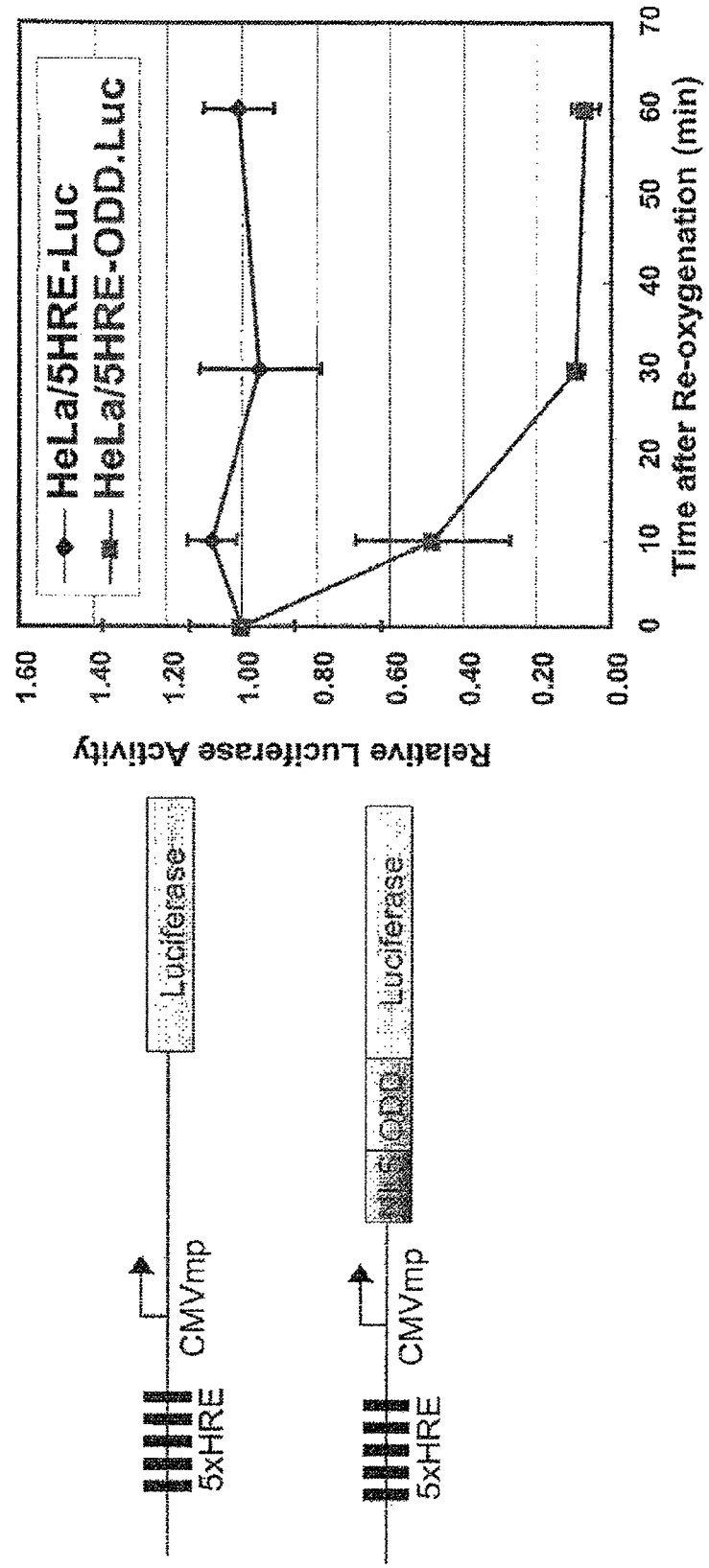

FIG. 4 Luciferase Activity Transition Through Re-Oxygenation after Hypoxic Treatment Expressions of the reporter gene when using 5HRE promoter alone and when using 5HRE combined with ODD were compared. Reporter change was investigated upon change from a hypoxic condition to an aerobic condition.

HeLa/5HRE-Luc cells and HeLa/5HRE-ODD-Luc cells were seeded on a 24-well culture dish ($1 \times 10^4$ cells/well), followed by incubation during 16 hours and subsequent hypoxic treatment for 18 hours. The cells were removed from the hypoxic chamber and were immediately transferred to a cycloheximide-containing culture medium, where re-oxygenation was carried out through culture in a 5% $CO_2$ incubator over 0, 10, 30 and 60 minutes. Thereafter, the culture was suctioned off, Passive Lysis Buffer (Promega Co.) was added in an amount of 10 µl/well, and then the wells were frozen at −80° C., after which cell extracts were collected through melting. A luciferase assay (Promega) was carried out using 20 µl of cell extract.

Luciferase activity was measured 0, 10, 30 and 60 minutes after re-oxygenation. The ratios of luciferase activity at the various points in time were calculated with respect to luciferase activity at 0 minutes, to yield relative luciferase activities. The results showed that when ODD is combined with 5HRE the reporter decreases faster, which enables better real-time capture of environmental changes.

Figure 5:
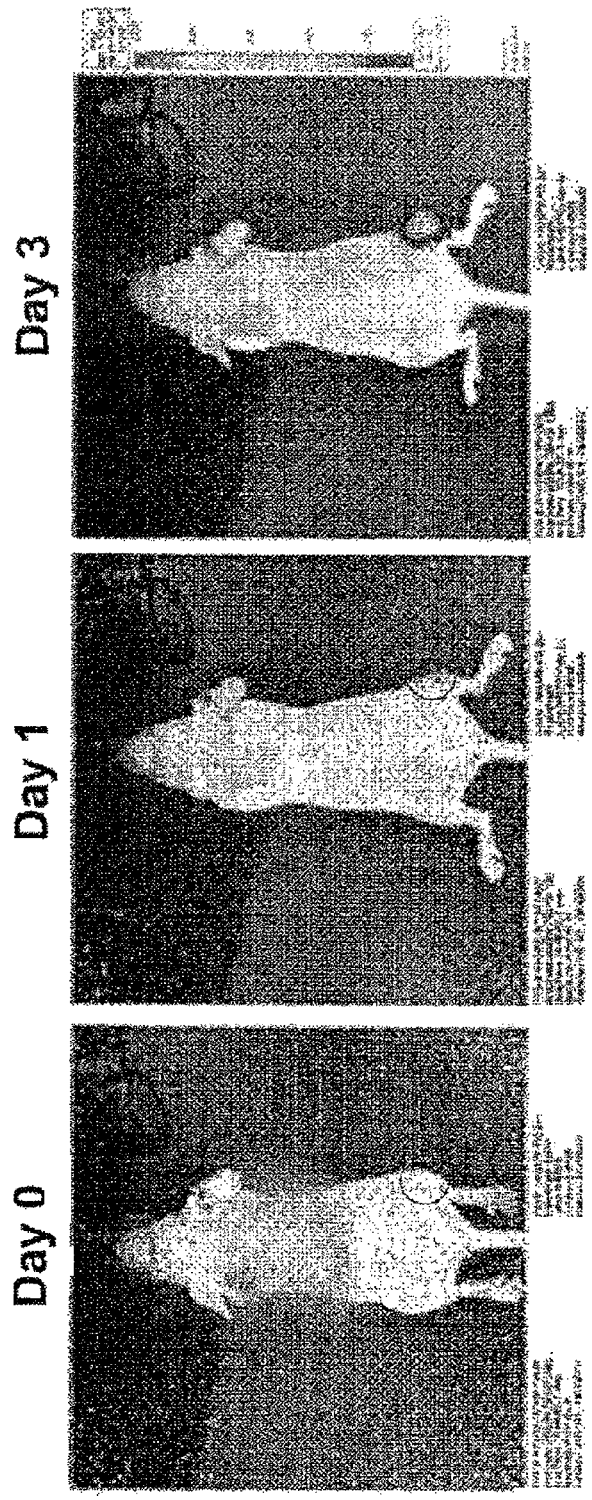

FIG. 5 Monitoring of Hypoxic Cancer Cells in a Solid Tumor (Graft)

In order to ascertain how good is the sensitivity with which cancer cells can be monitored in a hypoxic environment, human cancer cells having stably integrated therein a 5HRE-mp-NLS-ODD-Luciferase gene construct were grafted subcutaneously on the leg of a nude mouse, and then luciferase luminescence was monitored. $1 \times 10^6$ human cancer cells were grafted subcutaneously on the right leg (circle) of the nude mouse. No luminescence was observed immediately after graft owing to the aerobic environment at the time (image on the left). An image was already visible on the following day, and after three days the image was very clearly observable, although not as a tumor. Herein was captured luciferase luminescence in the hypoxic cancer cells of a solid tumor (image on the right).

FIG. 6 Enhancement of Luciferase Luminescence Through Ischemic Treatment

With a view to comparing the effect of hypoxia on expression induction of a reporter gene, expression induction was compared with that during a hypoxic state created by impaired blood flow through ligation, both in a tumor formed of cells having integrated therein a reporter gene with a 5HRE promoter alone, and a tumor formed of cells having integrated therein a reporter gene of a combination of 5HRE and ODD.

HeLa/EF-Luc was grafted subcutaneously on the left leg and HeLa/5HRE-Luc (upper series a to d) or HeLa/5HRE-ODD-Luc (lower series e to h) was grafted subcutaneously on the right leg. The amount of luciferase luminescence after 0, 2, 4 and 8 hours following leg ligation was measured. The results indicated that there were no substantial differences as regards the quickness of expression induction of the reporter gene in all the gene constructs. Upon impairment of blood flow on the right leg alone, following graft of tumor cells on both legs, images became enhanced only for the bound leg.

Figure 7:
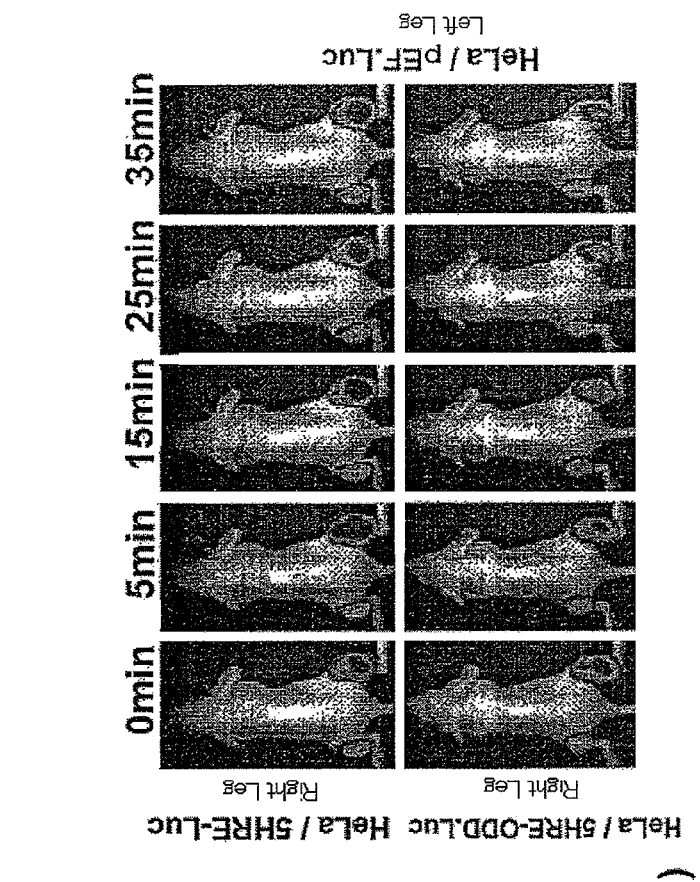
Figure 7:
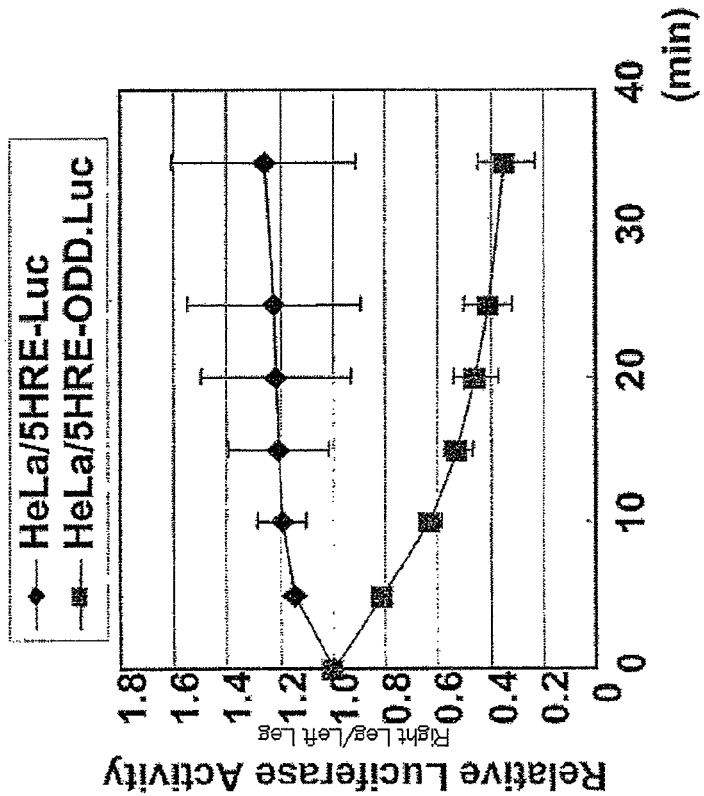

FIG. 7 Luciferase Luminescence Transition by Re-Oxygenation after Ischemic Treatment With a view to comparing next the expression change of the reporter as a result of re-oxygenation, the ligation of the tumor, in which a hypoxic state had been created by flow impairment through ligation, as in FIG. 6, was removed, to elicit blood flow recovery, after which the expression change of the reporter was compared.

HeLa/EF-Luc (internal control) cells were grafted on the left leg, and HeLa/5HRE-Luc (upper right series) or HeLa/5HRE-ODD-Luc (lower right series) cells were grafted on the right leg. Luciferin was administered intravenously after ligation of the right leg for 18 hours. After anesthesia, the ligation was removed, and the amount of luciferase luminescence was measured 0, 5, 15, 25 and 35 minutes following ligation removal.

The ratio of luciferase luminescence of the right leg vis-à-vis the amount of luciferase luminescence of the left leg was calculated for each measurement time, and then relative luciferase activities were calculated as the ratio of the values for each measurement time relative to the value at 0 minutes. The results indicated that, as in the experiment (FIG. 4) using culture cells, images did not change, even with re-oxygenation, where ODD was absent, but in the case of a combination of 5HRE and ODD, reporter decrease was fast and it was possible to capture better, in real time, changes in the environment, in vivo.

Figure 8:
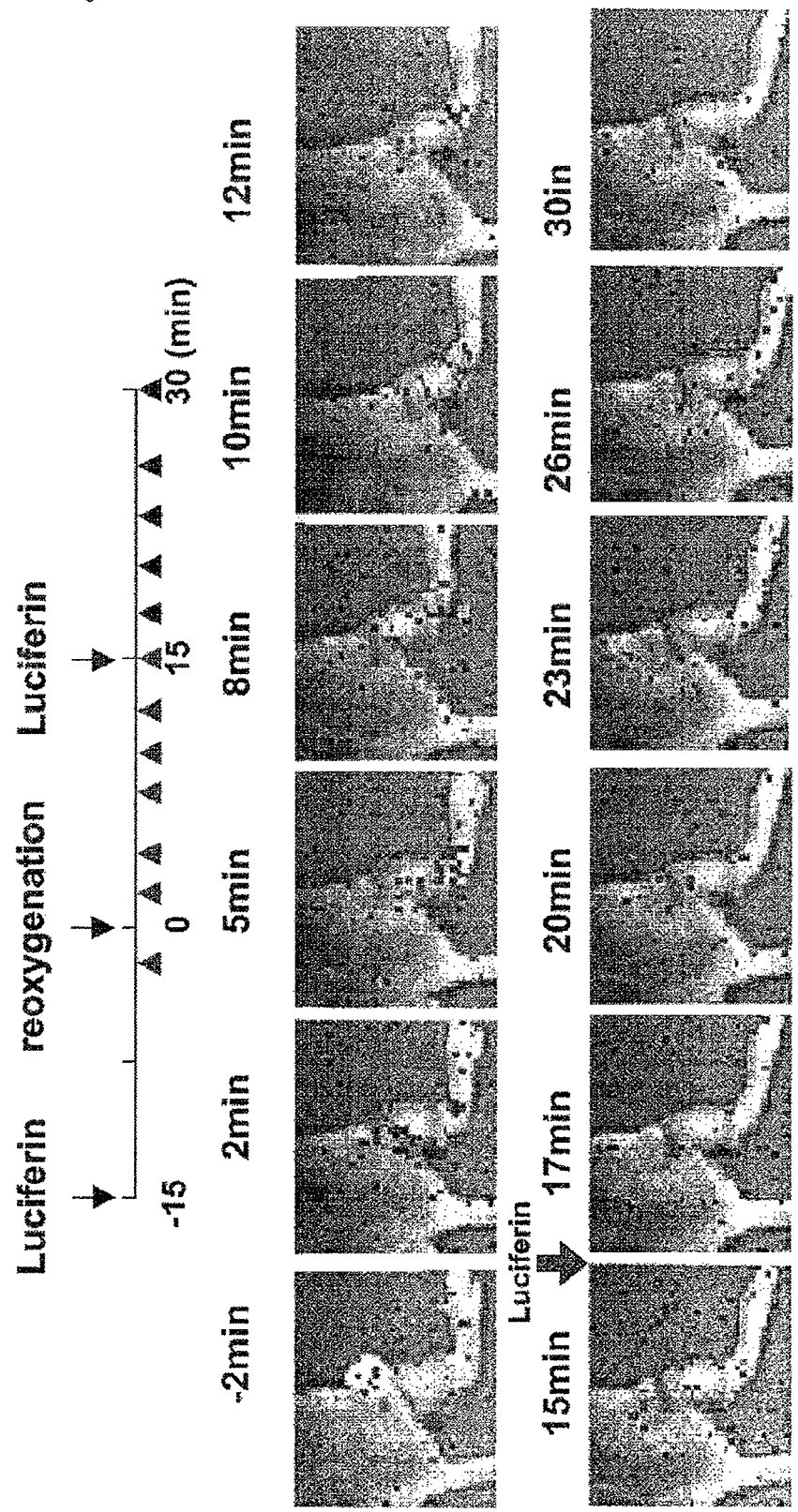

FIG. 8 Transgenic Mouse

The experiment conducted in FIG. 7 involved using cells having stably integrated therein 5HRE-mp-NLS-ODD-Luciferase. An experiment was conducted now, using a transgenic mouse, with a view to determining whether or not similar effects can be observed when the above gene construct is stably integrated in whole-body cells.

The right leg of a transgenic mouse was ligated for 16 hours. The mouse was anesthetized with isoflurane 11 minutes after administration of luciferin, and an image was taken 13 minutes after luciferin administration (−2 min). The ligation was removed 15 minutes after luciferin administration, to re-oxygenate thereby the right leg. Taking the moment of re-oxygenation as a reference (0 min), mouse images were taken 2, 5, 8, 10, 12 and 15 minutes after re-oxygenation, followed by immediate administration of supplementary luciferin, and further imaging at minutes 17, 20, 23, 26 and 30. The results showed that luciferin luminescence was observed only in the bound leg, and that luminescence faded quickly after ligation removal, with no luminescence being observed thereafter even upon a new administration of luciferin. This indicates that a hypoxic state can be monitored in a transgenic subject.

Figure 9:
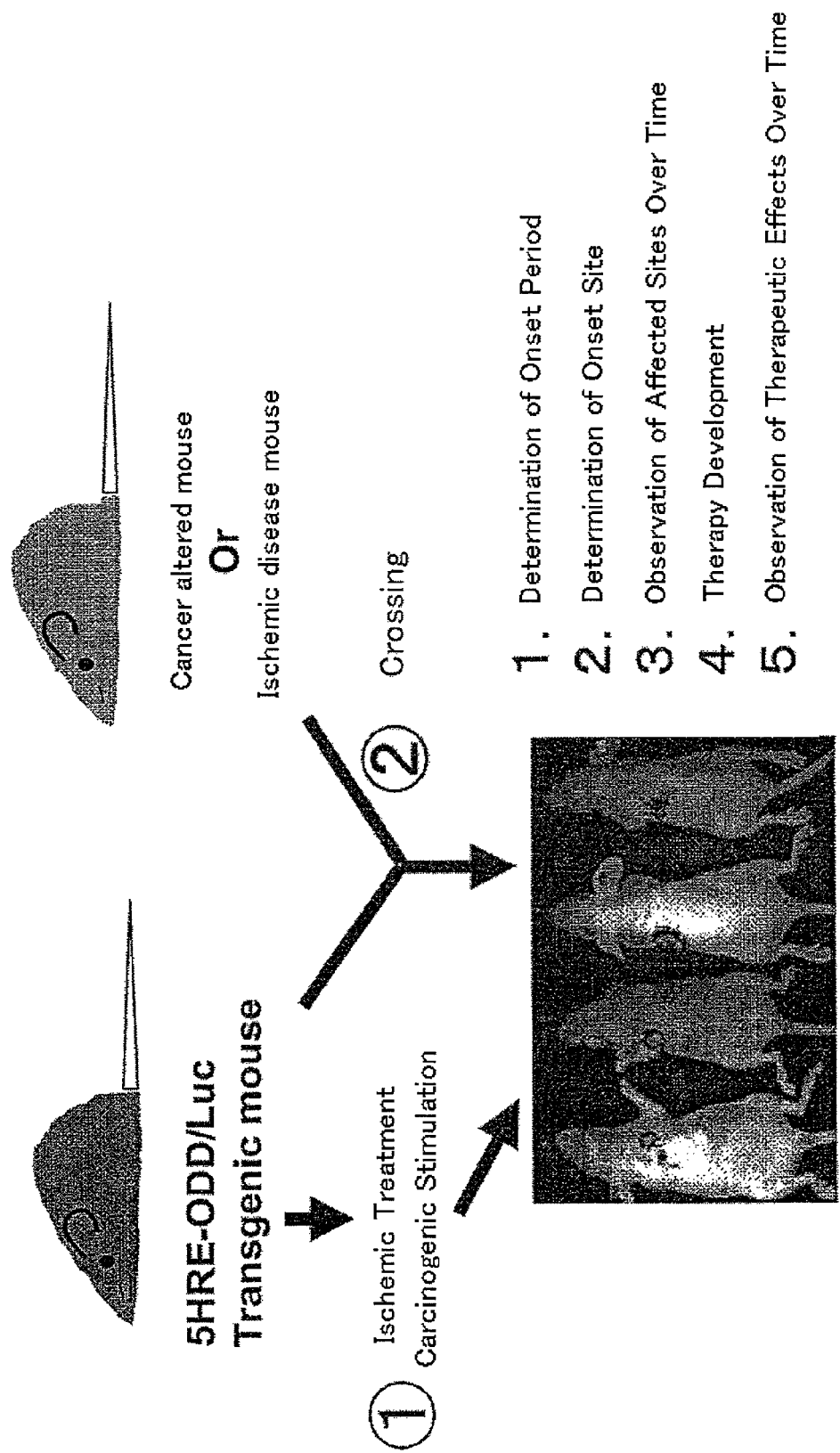

FIG. 9 illustrates a preferred embodiment of disease condition imaging using a transgenic mouse.

FIG. 10 With a view to investigating the relationship between the amount of protein taken up by a cell and oxygen concentration-dependent proteolysis efficiency mediated by the ODD domain, a NLS-ODD$_{3-0}$-β-galactosidase protein was fused to a protein transduction domain (PTD) which can introduce proteins freely into the cell through the cell membrane, the concentration of the protein was changed, then to the culture medium was added the protein having β-galactosidase activity corresponding to the unit number displayed on the cell culture solution, followed by incubation of the cells for 24 hours in an aerobic condition (20%) and a hypoxic condition (1%). The cells were then fixed with formalin, were washed thrice with PBS, and were then left to react with the solution containing the β-galactosidase substrate, to compare thereby β-galactosidase protein activity (i.e. the intracellular residual amount of β-galactosidase protein) in hypoxic versus aerobic conditions. Upon addition of protein up to 1.25 unit/ml, stabilized protein could be observed clearly only for the hypoxic cells. At greater concentrations, however, protein stabilization was observable also for the aerobic condition, which indicates that when protein is present in the cell beyond a certain amount, the limitations of the ODD-mediated degradation mechanism are exceeded, and the protein can no longer be degraded. This suggests that disease condition imaging resulting from hypoxia cannot be accurately carried out in tissues where the reporter gene is substantially expressed, on account of residual reporter, even when using a constitutive gene construct of promoter-NLS-ODD-reporter.

A: In each of the wells illustrated in the figure there were mixed 100 μl of a cell suspension comprising various HeLa/EF-Luc cells and 50pl of a luciferin solution (0.1 mg/ml). Immediately thereafter, chemiluminescence was imaged using an IVIS-200 system (Xenogen). As a result it was possible to observe in the order of $10^3$ luciferase expressing cells. B: on the basis of the experimental results in (A), the amount of chemiluminescence in each well was quantified using Living Image R2.50 (Xenogen). The results showed that the amount of chemiluminescence from $7.8 \times 10^2$ cells was significantly ($p<0.05$) larger than the amount of chemiluminescence from $3.9 \times 10^2$ cells. This indicates that the luciferase luminescence generated by an order of $10^2$ cells can be detected by the IVIS-200 system (average ±SD; n=2). C: On the back of a nude mouse there were grafted subcutaneously $1.0 \times 10^5$ HeLa/EF-Luc cells (left) and $1.0 \times 10^4$ HeLa/EF-Luc cells (right), followed by detection of chemiluminescence on the next day using the IVIS-200 system. It was shown that at least $1.0 \times 10^4$ luciferase luminescent cells can be detected in vivo.

Figure 12:
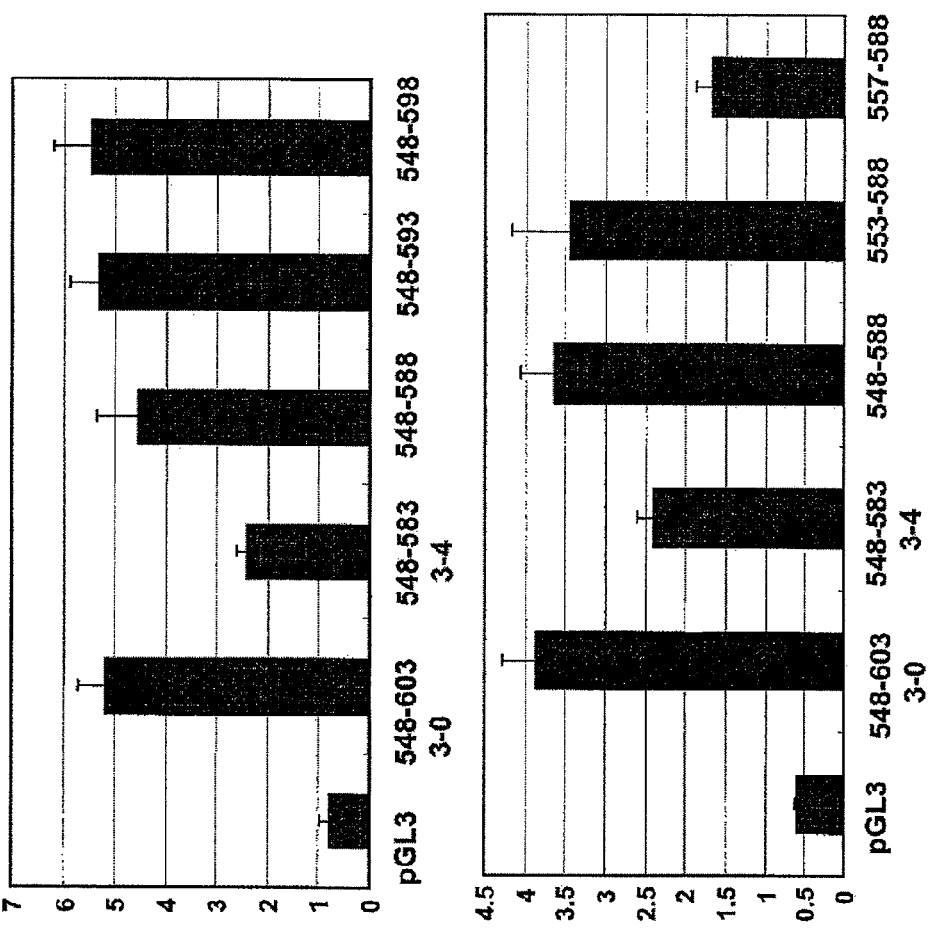

FIG. 12 Using as a template total RNA from a HeLa cell line derived from human cervical cancer, cDNA of the human HIF-1α gene was obtained through reverse transcription reaction with AMV reverse transcriptase XL. Using now the cDNA as a template, PCR was carried out combining the primers given in table 1 with ODD-Bgl-F3 and A588-Nco-anti, ODD-Bgl-F3 and A593-Nco-anti, ODD-Bgl-F3 and T598-Nco-anti, Q553-Bgl-sense and A588-Nco-anti, and L557-Bgl-sense and A588-Nco-anti. The DNA fragments were digested with BglII and NcoI, to yield, BglII- and NcoI-digested termini at the 5' terminus and the 3' terminus, respectively, and to integrate the DNA fragments into the plasmid vector manufactured through treatment of the pGL3/3-0 with BglII and NcoI. Through this gene recombination there were constructed a plasmid expressing the genes wherein various deleted DNA fragments of the ODD region (amino acid numbers 548-588, 548-593, 548-598, 553-588, 557-588 of HIF-1α), NLS, and luciferase are fused (respectively, pGL3/548-588, pGL3/548-593, pGL3/548-598, pGL3/553-588, and pGL3/557-588). Luciferase activity was measured in accordance with the same assay method illustrated in FIG. 1 using these plasmids. The plasmid DNA used was pGL3 promoter vector, pGL3/3-0, pGL3/3-4, pGL3/548-588, pGL3/548-593, pGL3/548-598, pGL3/553-588, and pGL3/557-588, denoted in the figure by pGL3, 548-603 (3-0), 548-583 (3-4) 548-588, 548-593, 548-598, 553-588, and 557-588, respectively. The results showed that all the fused proteins in which ODD was fused with luciferase were under stable control dependent on oxygen concentration. It was also seen that strong oxygen concentration dependency, similar to that resulting from the fusion of ODD3-0(548-603) with luciferase, could be achieved also by fusing the ODD553-588 region with luciferase.

BEST MODE FOR CARRYING OUT THE INVENTION

The invention allows imaging of hypoxic or diseased tissues at an extremely early stage, and enables hence elucidation of disease conditions or extremely effective screening of therapeutic agents for a disease.

Figure 11:
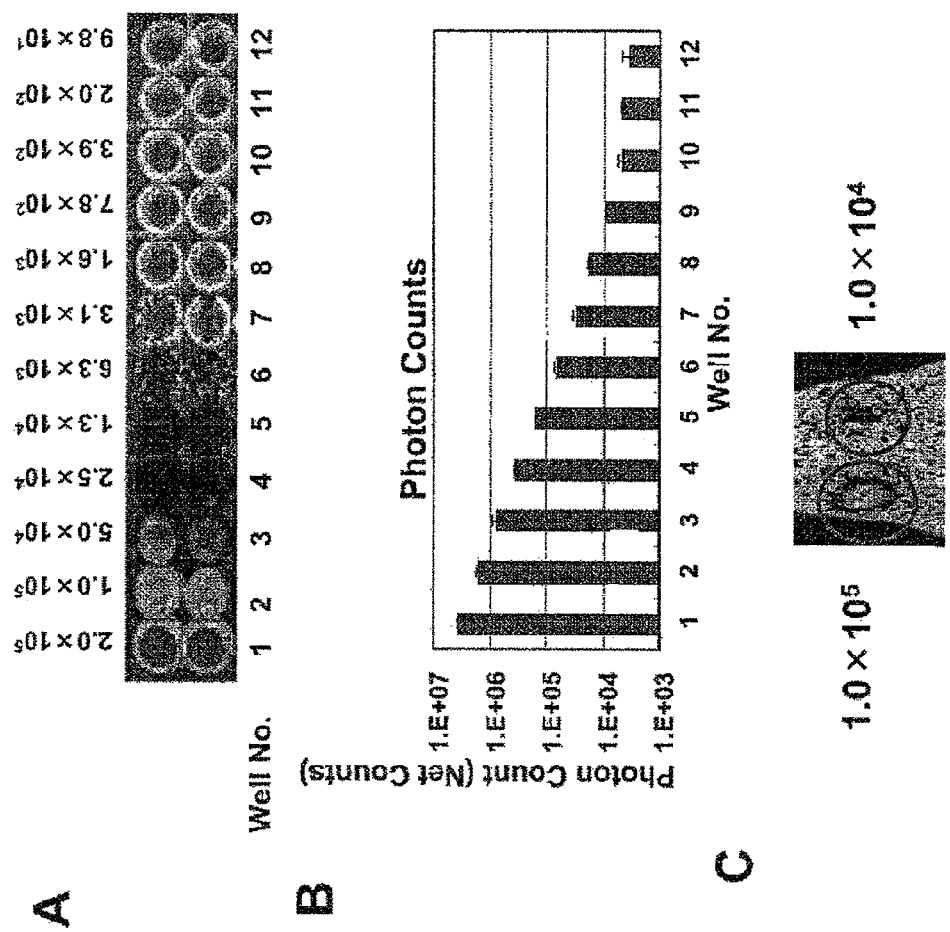

In FIG. 5, for instance, imaging of cancer becomes possible 1 day after grafting of as little as $1 \times 10^6$ cancer cells onto a nude mouse, while extremely sharp imaging can be carried out after 3 days, at the stage where the tumor cannot be observed. In FIG. 11, similarly, as little as $1 \times 10^4$ cancer cells can be detected.

Suitable imaging in accordance with the degree of severity of a condition (for instance, oxygen concentration, cancer cell count) can be carried out also using the gene construct of the present invention (FIGS. 6 through 8).

The transgenic mouse of the present invention, crossed with a disease model animal, allows imaging a disease of interest. This is highly useful, for instance, in the determination of onset periods and onset sites, observation of affected sites over time, therapy development, and observation of therapeutic effects over time.

As illustrated in FIG. 9 of the present invention, disease condition imaging can be carried out by crossing a transgenic mouse of the present invention with another disease mouse (for instance, a cancer altered mouse or an ischemic disease mouse), or by carrying out an ischemic treatment or carcinogenic stimulation.

In the description and claims of the present invention, unless otherwise stated, the terms ODD domain (oxygen dependent degradation domain), HIF-1 binding domain (HRE: hypoxia-responsive element), minimal promoter (mp), and nuclear localizing signal (NLS) as used herein denote the respective polynucleotides coding for the same.

The term "disease condition" encompasses broadly not only a disease state but also an initial adverse condition that leads to the disease. In the case of a cancer condition, for instance, the latter includes an aggregate of several tens of cancer cells that can be imaged in accordance with the present invention, while in an ischemic "disease condition", such as angina pectoris, myocardial infarction, brain stroke, ischemic and reperfusion injury, the term encompasses broadly not only clogging of blood vessels but also a systemic or local impairment of blood flow caused by atherosclerosis or thickening of vascular endothelial cells.

In the present invention, reporter genes include, for instance, β-galactosidase genes, luciferase genes (blue, red, orange, green and the like), (green, yellow, cyan, red, blue) fluorescent protein genes (GFP, YFP, CFP, BFP, DsRed, DsRed2), alkaline phosphatase genes, horseradish peroxidase genes, or chloramphenicol acetyl transferase genes. Luciferases are particularly preferred herein on account of their sensitivity. Among luciferases, those having long-wavelength luminescence, such as red or orange luminescence, are preferred on account of being readily identifiable in deep sites. Sources of luciferases include, for instance, luminous insects such as Photinus pyralis, luminescent rice bug, and other bioluminescent organisms such as Diplocardia, Latia, Acanthephyra purpurea, Rhagophthalmus ohbai, Cypridina, Renilla, railroad worm, dinoflagellates, Aequorea coerulescens (aequorin) and the like.

Hypoxia responsive promoters denote both elements (enhancers) whose expression is induced during hypoxia and elements that promote transcription through binding with RNA polymerase during hypoxia.

Elements that can induce transcription activity during hypoxia include, although not limited thereto, for instance HIF1 responsive elements (enhancers). A preferred concrete example thereof is an HRE (hypoxia responsive element) having an HIF1 binding domain. The HRE is preferably used as plural HREs spliced in tandem. The number of HREs spliced in tandem ranges, for instance, from 2 to 5.

When an element in which there are 5 HREs in tandem (5HRE) is hypoxia-induced, expression increases abruptly after two hours (in particular, after four hours), as illustrated in FIG. 2.

Known elements that promote transcription through binding with RNA polymerase are many and widely used, and include, for instance, CMVmp (cytomegalovirus minimal promoter).

The ODD domain (oxygen dependent degradation domain) may comprise a polynucleotide coding for the region of amino acids 401 to 603 in the amino acid sequence of human HIF-1α of sequence number 1. FIG. 1 and FIG. 12 illustrate the results of measurements of the luciferase activity of ODD domains having various lengths, carried out for elucidating the indispensable portions of the ODD domain.

The ODD domain:

(i) comprises preferably, in particular, a polynucleotide coding for the 557 to 574 amino acid region;

(ii) comprises more preferably a polynucleotide coding for the 553 to 556 and 575 to 588 amino acid regions;

(iii) may comprise a polynucleotide coding for the 548 to 552 and 589 to 603 amino acid regions; and (iv) may comprise, but preferably does not, a polynucleotide coding for the 401 to 547 amino acid region.

Other than an ODD domain derived from the human HIF-1α of sequence number 1, there may be used also human HIF-2α, HIF-3α or the like, or an ODD domain derived from HIF-1α homolog of a non-human organism, such as mice or rats. A polypeptide may be used instead of HIF-1α-derived ODD, provided that the polypeptide is controlled so as to be degraded in aerobic conditions and, conversely, stabilized in hypoxic conditions.

The combination of an ODD domain and a hypoxia inducible promoter is extremely important in the present invention.

As illustrated in FIG. 3, a simple hypoxia inducible promoter (for instance, a promoter combining 5×HRE and cytomegalovirus minimal promoter (CMPmp)) by itself elicits gene expression, although small, in aerobic conditions, and hence the induction ratio, which denotes the amount of expression during hypoxia divided by the amount of expression during aerobic conditions, is of about 300-fold in this case. On the other hand, expressed promoter protein is degraded quickly, within several minutes, by including an ODD domain (and, preferably, also NLS) in the combination. This affords hence a gene construct in which the promoter gene is virtually unexpressed in aerobic conditions (level identical to background). Induction ratios of about 1200-fold can thus be achieved as a result. This allows, in consequence, to increase specificity to hypoxic sites, and enables accurate monitoring (for instance, through imaging) of disease sites resulting from hypoxia.

A reporter protein having no ODD domain polypeptide persists stably also in aerobic conditions, whereas a reporter protein further combined with an ODD domain polypeptide (and, preferably, also NLS) is degraded quickly, within several minutes, when exposed to aerobic conditions. This phenomenon is observed both at the cellular level (FIG. 4) and the whole-organism level (FIG. 7).

According to FIG. 3, the induction ratio, which denotes the amount of expression during hypoxia divided by the amount of expression during aerobic conditions, drops from about 1200-fold to about 300-fold when ODD is absent, which impairs considerably imaging sharpness of the disease sites. Patent documents 1 and 2 disclose a combination of a reporter gene product and a hypoxia inducible promoter (HRE). For recognizing a hypoxic state, increasing as much as possible the amount of expression during hypoxia by combining an HRE with a reporter gene has been a conventional practice hitherto. The inventors found out that, when an ODD is also included in the combination, the amount of expression decreases through partial degradation of the reporter gene, but the induction ratio increases, which enables sharp imaging of disease sites. The present invention reveals for the first time that, combining a hypoxia inducible element (for instance, HRE), which is an element that increases the amount of expression of a reporter gene during hypoxia, with an ODD, which reduces the amount of expression of the reporter gene, has the effect of enhancing the imaging efficiency of disease sites.

Preferably, the gene construct of the present invention comprises further a nuclear localizing signal (NLS). An NLS denotes an amino acid sequence that is necessary for confining proteins in the nucleus of a eukaryotic cell, which possesses a nuclear membrane inside the cell. The NLS is not particularly limited, provided that it has activity for localizing proteins in the nucleus, and may be, for instance, preferably an NLS derived from the SV40 large-T antigen (a polynucleotide coding for the 126 to 132 amino acid region of the large-T antigen; Proc. Natl. Acad. Sci. (1989) 86: 9327-9331), or an NLS of HIF-1α.

The gene construct of the present invention has preferably the following structure: (HIF-1 binding domain)-(mp)-(NLS)-(ODD domain)-(reporter gene). The various polynucleotides of the HIF-1 binding domain, mp, NLS, ODD domain and the reporter gene may be fused directly to one another, or may be fused via a suitable nucleotide sequence.

A transformant cell can be obtained by integrating the gene construct of the present invention into a mammalian cell. Integration of the gene construct of the present invention into an animal cell, in particular into a mammalian cell, can be carried out using, for instance, the calcium phosphate method (Chen and Okayama method: Mol Cell Biol. 1987 August; 7(8): 2475-52).

Examples of hosts in which the gene construct of the present invention can be transfected include, for instance, animal cells from mammals (humans, monkeys, dogs, cows, horses, sheep, pigs, rabbits, mice, rats, guinea pigs, hamsters and the like), insects, birds (chickens and the like), reptiles (for instance, frogs and the like), or fish, as well as in eukaryotic cells such as yeast or the like, but preferably mammalian cells.

The transformant of the present invention enables imaging of intracellular hypoxic states, and is useful for the screening of drug candidate compounds having a protective effect against hypoxia. In the present invention, the term "candidate compound" encompasses broadly, in addition to low-molecular weight compounds, also natural or synthetic substances (monomers, oligomers and polymers) such as proteins, nucleotides (oligomers and polymers), peptides (oligomers and polymers), saccharides (monosaccharides, disaccharides, polysaccharides and the like), glycolipids, glycoproteins and the like.

Transgenic nonhuman mammal animals can be created in accordance with known methods used ordinary in the manufacture of transgenic animals (see, for instance, "Current Manual for Animal Cell Experiments" LIC, Chapter 7, pages 361 to 408 (1990)). In the case of a transgenic mouse, for instance, mouse embryonic stem cells (ES cells) are transformed using an expressing vector comprising the gene construct of the present invention. A founder mouse is obtained through microinjection of such transformant ES cells into a fertilized egg (blastocyst) obtained from another mouse. The founder mouse is backcrossed twice with another mouse (for instance, although not limited thereto, a BALB/c mouse), to obtain thereby a transgenic mouse of the present invention (heterozygous, i.e. a mouse having the gene construct of the present invention in only one chromosome). A homozygous transgenic mouse can be obtained by further crossing between heterozygous transgenic mice.

A transgenic mouse having introduced therein a (5×HRE)-(CMVmp)-(NLS)-(548 to 683 ODD domain)-(firefly luciferase gene) gene construct was deposited domestically, on Mar. 8, 2005, with the International Patent Organism Depositary, National Institute of Advanced Industrial Science and Technology, under accession number "FERM P-20451", and internationally thereafter, on Feb. 22, 2006, with the International Patent Organism Depositary, National Institute of Advanced Industrial Science and Technology, under accession number "FERM ABP-10537".

Using normal mice as another mouse employed in the process for manufacturing transgenic mice allows real-time detection of hypoxic sites and dysfunctional sites in transgenic mice.

Mice in which a disease condition can be observed in real time can be obtained by crossing another mouse employed in the process for manufacturing transgenic mice, or hetero- or homo-transgenic mice with disease model mice and/or gene-altered mice (other transgenic mice, knockout mice, and mice that, for instance, develop spontaneously conditions such as ischemic brain vessel lesions, ischemic heart disease, ischemic atherosclerosis, solid cancer and the like).

A method for manufacturing a transgenic mouse has been described above, but a nonhuman mammal of the present invention can be obtained also, in the same way as in the case of a mouse, by using a nonhuman mammal other than a mouse.

When using luciferase as the reporter gene of the present invention, administering luciferin to the nonhuman mammal allows recognizing luminescence at hypoxic or diseased sites. Luciferin can be suitably administered through intravenous, intraperitoneal, intramuscular or subcutaneous injection, or can be continuously released using a drug delivery system.

In the luciferin-luciferase system, hypoxic or diseased sites can be recognized by housing the nonhuman mammal of the present invention, having a luciferase gene as a reporter gene, in a box that allows detection of the specific wavelengths of the luciferin-luciferase system, and by observing the emitted luminescence. Luminescent proteins such as GFP, YFP, CFP, BFP, DsRed, DsRed2 and the like can also be recognized in the same way as luciferase.

Specific examples of boxes that can be used herein include, for instance, systems IVIS-100, IVIS-200 (Xenogen Co.), Photoimager (BIOSPACE) and the like.

An enzymatic reaction can be imaged, in the form of a fluorescent phenomenon, on the basis of the change in fluorescence wavelength through substrate phosphorylation in the case of alkaline phosphatase, the fluorescence resulting from the luminol reaction in the case of horseradish peroxidase, and/or by adding a light-emitting marker to a protein as a substrate in the case of other enzymes (β-galactosidase or chloramphenicol acetyl transferase) and by modifying a protein so that the fluorescence wavelength changes as a result of an enzymatic reaction (for instance, as a result of changes such as substrate scission or the like).

In terms of imaging sensitivity, luciferase is particularly preferred as the reporter gene.

The screening method of the present invention is performed by administering various compounds to a transformant cell (transformant) or a transgenic nonhuman mammal of the present invention, and observing changes in expression of a reporter gene.

For instance, the efficacy of a compound, in particular a drug candidate compound, can be studied with precision by administering the compound to a transgenic nonhuman mammal having the disease, and by observing then, preferably in real time, how the disease condition changes.

The administered compound may be, broadly, a protein (including a hormone, antibody, enzyme, receptor or the like), a nucleic acid (DNA, RNA) or a substance and/or biologically active substance that works with these compounds (including low molecular weight compounds and high molecular weight compounds). The administered compound may also be a compound for ascertaining toxic effects.

The reporter gene may be integrated as only one gene or as two, three, four or more genes at the same time.

EXAMPLES

The present invention is explained in detail next based on examples.

(1) Construction of Recombinant DNA (5HRE-mp-NLS-ODD-Luciferase)

An expression vector comprising the recombinant DNA possessed by the transgenic mouse of the present invention was constructed in accordance with the following procedure.

An NLS-ODD DNA fragment (DNA fragment coding for NLS-ODD548-603) was amplified by PCR using a pCH/3-0 plasmid (Harada et al. 2002 Cancer Res.) as a template, and employing a NLS-Nco-sense primer; 5'-AAC CAT GGC GCC TAA GAA GAA GAG GAA G-3', and an ODD-Nco-anti primer; 5'-AAC CAT GGT CTG CTG GAA TAC TGT AAC TG-3'. After NcoI digestion, this DNA fragment was inserted at the NcoI position of the 5HRE-hCMVmp-Luc plasmid (Shibata et al. 2000, Gene Ther.; hereinafter pGL3/5HRE-Luc), to construct thereby a plasmid pGL3/5HREp-NLS-ODD-Luciferase for expressing an NLS-ODD-luciferase fused protein under the control of a 5HRE promoter. A KpnI-XbaI fragment of this plasmid and the pGL3/5HRE-Luc plasmid were inserted at the KpnI-XbaI position of pEF/myc cyto (Invitrogen) to construct pEF/5HREp-ODD-Luc and pEF/5HRE-Luc, respectively.

A plasmid vector that constitutively expresses luciferase portion was constructed in accordance with the following procedure. The cDNA of the luciferase gene was obtained by PCR using Luc-Bam-sense primer 5'-AAG GAT CCA CCA TGG AAG ACG CCA AA-3', and Luc-RV-anti primer 5'-TTG ATA TCT TAC ACG GCG ATC TTT CC-3', and employing pGL3 promoter vector as a template. After digestion with BamHI and EcoRV, the cDNA was inserted at the BamHI-EcoRV position of the pEF6/Myc-His B plasmid (Invitrogen), to construct a plasmid pEF/Luc that expresses luciferase constitutively.

(2) Cell Culture

HeLa cells derived from human cervical cancer, obtained from ATCC, were cultured in Dulbecco's Modified Eagle Medium: D-MEM to which there had been added 100 unit/ml of penicillin, 100 µg/ml of streptomycin, and 10% fetal bovine serum.

(3) Isolation of Cells Transfected With the Reporter Gene pEF/Luc, pEF/5HRE-Luc and pEF/5HRE-ODD-Luc were transfected into the HeLa cells using the calcium phosphate method. With a view to obtaining cell strains in which each plasmid was stably integrated in the genomic DNA, the cells were cultured, for 10 days following gene transfection, in a selective culture medium containing 400µg/ml of G418, and then the formed colonies were isolated. In the experiments there was used a clone (HeLa/EF-Luc) that expresses luciferase constitutively, among isolated clones in which pEF/Luc was transfected. In the experiments there were also used the clones (HeLa/5HRE-Luc and HeLa/5HRE-ODD-Luc) having a high luciferase inducing power through hypoxic treatment, among the clones obtained by transfection of pEF/5HRE-Luc or pEF/5HRE-ODD-Luc into HeLa cells.

(4) Measurement of Luciferase Activity

The following experiment was carried out for determining the hypoxia responsiveness of a HIF-1-dependent promoter comprising 5HRE. HeLa/5HRE-Luc cells were inoculated in a 24-well culture dish ($1 \times 10^4$ cells/well), and were incubated for 16 hours. The cells were incubated thereafter for 0, 1, 2, 4, 8 and 16 hours under aerobic conditions (20% $O_2$) and hypoxic conditions ($\leq 1\%$ $O_2$). Thereafter, the cells were washed with phosphate buffered saline (PBS), were lysed with 100 µl of passive lysis buffer (Promega, Madison, Wis.), and then 10 µl luciferase activity was measured using a luciferase assay kit (Promega), to yield the net counts plotted in the graph of FIG. 2. The HIF-1α protein expressed in the cells was determined by means of the western blot method (FIG. 2 bottom). Specifically, the cells conditioned in accordance with the above method were cultured in hypoxic conditions. After 0, 1, 2, 4, 8 and 16 hours, the cells were dissolved directly in one 100 µl loading buffer inside a hypoxic chamber, then 20 µl of the solution was electrophoresed in 7.5% SDS-polyacrylamide gel. The gel was transferred to a PVDF film (Amersham Biosciences, Piscataway, N.J.), then the HIF-1α protein on the gel was labeled with monoclonal anti-HIF-1α antibody (BD Bioscience Pharmingen, San Diego, Calif.), and anti mouse IgG horseradish peroxidase linked with whole antibody (Amersham Bioscience), followed by identification of the labeled protein using an ECL-PLUS system (Amersham Bioscience). The results are illustrated in FIG. 2.

The following experiment was carried out to compare hypoxia responsiveness when the reporter gene is firefly luciferase alone and when the reporter gene has NLS-ODD fused to firefly luciferase. HeLa cells were seeded on a 24-well culture dish (10000 cells/well). After 16 hours of incubation, pGL3, pGL3/5HRE-Luc or pGL3/5HREp-NLS-ODD-Luciferase (0.4 µg/well) was transfected using Polyfect Transfection Reagent (QIAGEN). A plasmid pRL/CMV (Promega) for constant expression on Renilla luciferase was also transfected simultaneously herein as an internal control (0.04 µg/well). The culture medium was replaced 24 hours after gene transfection, followed by further culture over 18 hours under aerobic or hypoxic conditions (oxygen concentration<0.02%). After suctioning off the culture medium, the cell extracts were collected using 100 ml of Passive Lysis Buffer (Promega), and a dual luciferase assay was carried out in accordance with the accompanying instructions. The results are illustrated in FIG. 3.

The Promega dual assay system was used only for the experiments of FIGS. 1 and 3. In order to express temporarily the genes coding for each of the constructs, there was transfected herein simultaneously a constant amount of gene coding for Renilla luciferase, with a view to correct the difference caused by the difference in transfection efficiency of the genes, then the two luciferase (firefly luciferase and Renilla luciferase) activities were measured, and the ratio thereof was used for activity evaluation.

In other experiments, activity was measured and evaluated based on the amount of expression of firefly luciferase alone.

FIG. 3 top: The "ratio of firefly luciferase activity relative to Renilla luciferase activity" was calculated for hypoxic conditions and aerobic conditions. The induction power (Induction ratio: Hypo/Aero) was then determined as the ratio between the calculated value for hypoxic conditions relative to the calculated value for aerobic conditions.

FIG. 3 bottom: The activity of firefly luciferase under aerobic conditions was taken as the background (net count under Aero) under aerobic conditions.

The way in which the activity of firefly luciferase, which is herein the reporter gene, changed versus oxygen concentration (from hypoxia to aerobic conditions) was investigated using human cancer cell lines Hela/5HRE-Luc and HeLa/5HRE-ODD-Luc having stably therein pGL3/5HRE-Luc or pGL3/5HREp-NLS-ODD-Luciferase.

HeLa/5HRE-Luc cells and HeLa/5HRE-ODD-Luc cells were inoculated in a 24-well culture dish ($1 \times 10^4$ cells/well), and were incubated for 16 hours. The cells were subjected then to a hypoxic treatment for 18 hours. Immediately after being removed from the hypoxic chamber, the cells were transferred to a cycloheximide-containing culture medium where re-oxygenation was carried out through culture in a 5% $CO_2$ incubator over 0, 10, 30 and 60 minutes. Thereafter, the culture was suctioned off, Passive Lysis Buffer (Promega Co.) was added in an amount of 10 µl/well, then the wells were frozen at –80° C., after which cell extracts were collected through melting. A luciferase assay (Promega) for luciferase activity was carried out using 20 µl of cell extract. The ratios of luciferase activity at the various points in time were calculated with respect to luciferase activity at 0 minutes, to yield relative luciferase activities.

The results are illustrated in FIG. 4.

(5) Creation of a Tumor Model

After trypsinization, the cells were washed with cold PBS and were suspended in PBS to a concentration of ($1 \times 10^6$ cells/100 µl). This cell suspension was grafted subcutaneously onto the leg of 6-week old female BALB/c nu/nu mouse.

FIG. 5 illustrates the results of imaging on the obtained model mouse.

(6) In vivo Imaging

HeLa/EF-Luc was grafted subcutaneously on the left leg and HeLa/5HRE-Luc or HeLa/5HRE-ODD-Luc was grafted subcutaneously on the right leg. 10 days after grafting, the right leg was ligated, then the mouse was immediately placed in an anesthesia device (Xenogen Co) filled with isoflurane gas. The mouse was administered iv 50 mg/kg of luciferin 0, 2, 4 and 8 hours after anesthesia, then chemiluminescence was detected using an IVIS-100 system (Xenogen Co). The obtained images were analyzed using Living Image R2.50 (Xenogen).

The results are illustrated in FIG. 6.

The mouse was administered 50 mg/kg iv 18 hours after ligation of the right leg. The mouse was then placed in an anesthesia device (Xenogen Co) filled with isoflurane gas once 12 minutes had elapsed since administration. The ligation was removed 3 minutes afterwards, and then chemiluminescence was detected 0, 5, 15, 25 and 35 minutes thereafter.

The results are given in FIG. 7.

In vivo imaging using a 5HRE-mp-NLS-ODD-Luciferase transgenic mouse was carried out as described below.

Firstly, the right leg of the transgenic mouse was kept ligated for 16 hours. After 11 minutes since luciferin administration, the mouse was anesthetized with isoflurane, and an image was taken 13 minutes after luciferin administration. The ligation was removed 15 minutes after luciferin administration, to re-oxygenate thereby the right leg. Taking the moment of re-oxygenation as a reference (0 min), mouse images were taken 2, 5, 8, 10, 12 and 15 minutes after re-oxygenation. The luminescence of the reporter protein decreased and faded over time. This was followed by immediate administration of supplementary luciferin, in order to rule out that the image observed theretofore was not a false positive image caused by hemorrhage or the like, with further imaging at minutes 17, 20, 23, 26 and 30. Once having disappeared after re-oxygenation, the reporter protein could not be detected a second time.

The results are illustrated in FIG. 8.

(7) Manufacture of a Gene-Manipulated Animal

A fertilized egg B6C3F2 obtained through natural crossing of female B6C3F1× male B6C3F1 was used for manufacturing a genetically altered animal. The relevant gene fragment (a Xho1-Sall fragment of pGL3/5HREp-NLS-ODD-Luciferase, about 1.7 kbp; 5HRE-CMVmp-NLS-ODD (548-603)—(Firefly luciferase gene)) was electrophoresed and then recovered and purified from 0.6% agarose gel, followed by dissolution in TRIS 10 mM, EDTA 0.1 mM ($T_{10}E_{0.1}$) to a concentration of 500 copy/pl. A 1000 copy equivalent amount per pro-nuclear mouse embryo was injected by microinjection (Methods in Enzymology Vol. 225, Guide to Techniques in Mouse Development), then the observable surviving fertilized eggs were implanted on the oviduct of a pseudo-pregnant 0.5 dpc ICR foster mother, to obtain offspring (founder transgenic) 19 days later, through cesarean section. A PCR gene analysis of the obtained offspring yielded positive for the gene of interest. A line was begun on the basis of this gene-positive individual, to establish the transgenic mouse of the present invention.

Fertilized eggs were prepared through external insemination using a wild (C57BL/6J) female and a hybrid male N1 individual having a hetero transgene, obtained through mating of the founder transgenic mouse (B6C3F2) with a BALB/c. The individuals obtained after fusion and implantation of the obtained fertilized eggs possessed and lacked the transgene in a proportion of 1:1. Fertilized eggs of the obtained transgenic mouse (HOL-A) were deposited domestically, on Mar. 8, 2005, with the International Patent Organism Depositary, National Institute of Advanced Industrial Science and Technology, under accession number "FERM P-20451", and internationally thereafter, on Feb. 22, 2006, with the International Patent Organism Depositary, National Institute of Advanced Industrial Science and Technology, under accession number "FERM ABP-10537".

REFERENCES

Shibata T, Giaccia A J, Brown J M (2002). Hypoxia-inducible regulation of a prodrug-activating enzyme for tumor-specific gene therapy. Neoplasia. 4:40-48.

Harada H, Hiraoka M, Kizaka-Kondoh S (2002). Antitumor effect of TAT-oxygen-dependent degradation-caspase-3 fusion protein specifically stabilized and activated in hypoxic tumor cells. Cancer Res. 62:2013-2018.

TABLE 1

| Primer name | Sequence |
| --- | --- |
| ODD-Bgl-F0 | 5'- AAA GAT CTG CCC CAG CCG CTG GAG -3' |
| ODD-Bgl-F1 | 5'- AAA GAT CTT TGG CAA TGT CTC CAT -3' |
| ODD-Bgl-F2 | 5' AAA GAT CTC CTA GTC CTT CCG ATG -3' |
| ODD-Bgl-F3 | 5'- AAA GAT CTA ACC CAT TTT CTA CTC -3' |
| ODD-Bgl-F4 | 5'- AAA GAT CTC AGT TGT CAC CAT TA -3' |
| ODD-Nco-R0 | 5'- AAC CAT GGT CTG GAA TAC TGT AAC -3' |
| ODD-Nco-R1 | 5'- AAC CAT GGT ATT TAT ATT CTG TAA -3' |
| ODDNco-R2 | 5'- AAC CAT GGT TGT CTG ATC CTG AAT C -3' |
| ODD-Nco-R3 | 5'- AAC CAT GGT CTT TGC TTC TGT GTC -3' |
| ODD-Nco-R4 | 5'- AAC CAT GGT TAA TGG TGA CAA CTG -3' |
| A588-Nco-anti | 5' AAC CAT GGT TGC GGA ACT GCT TTC TAA 3' |
| A593-Nco-anti | 5' AAC CAT GGT TGC GCT TTC AGG GCT TGC 3' |
| T598-Nco-anti | 5' AAC CAT GGT TGT GCT TTG AGG ACT TGC -3' |
| Q553-Bgl-sense | 5'- AAA GAT CTC AGG ACA CAG ATT TAG AC -3' |
| L557-Bgl-sense | 5'- AAA GAT CTT TAG ACT TGG AGA TGT TAG -3' |

| | | |
| --- | --- | --- |
| 0-1 | Form PCT/RO/134 (SAFE) Indications Relating to Deposited Microorganism(s) or Other Biological Material (PCT Rule 13bis) | |
| 0-1-1 | Prepared using | JPO-PRIOR APPLICATION SPECIFICATION 0332 |
| 0-2 | International Application No. | PCT/JP2006/304701 |
| 0-3 | Applicant's or agent's file reference | P06-22 |
| 1 | The indications made below relate to the deposited microorganism(s) or other biological material referred to in the description on: | |
| 1-1 | Paragraph | 0053, 0082 |
| 1-3 | Identification of deposit | |
| 1-3-1 | Name of depositary institution | International Patent Organism Depositary (IPOD), National Institute of Advanced Industrial Science and Technology |
| 1-3-2 | Address of depositary institution | Postal code 305-8566, Central 6, 1-1-1 Higashi, Tsukuba, Ibaraki, Japan |
| 1-3-3 | Date of deposit | Mar. 8, 2005 |
| 1-3-4 | Accession number | IPOD FERM ABP-10537 |
| 1-5 | Designated States for Which Indications are Made | All designated States |

For Receiving Office Use Only

| | | |
| --- | --- | --- |
| 0-4 | | This form was received with the international application: (yes or no) |
| 0-4-1 | | Authorized officer |

For International Bureau Use Only

| | | |
| --- | --- | --- |
| 0-5 | | This form was received by the international Bureau on |
| 0-5-1 | | Authorized officer |

The invention claimed is:

1. A gene construct which has a reporter gene integrated under the control of a hypoxia responsive promoter, and in which an ODD domain (oxygen dependent degradation domain) is fused in-frame to the reporter gene.

2. The gene construct according to claim 1, wherein the hypoxia-responsive promoter has a HIF-1 binding domain (HRE: hypoxia responsive element).

3. The gene construct according to claim 1, wherein the hypoxia-responsive promoter has a minimal promoter (mp).

4. The gene construct according to claim 1, wherein the reporter gene is a luciferase gene.

5. The gene construct according to claim 1, further comprising a nuclear localizing signal (NLS).

6. The gene construct according to claim 5, comprising a (HIF-1 binding domain)-(mp)-(NLS)-(ODD domain)-(reporter gene) structure, wherein the (HIF-1 binding domain)-(mp)-(NLS)-(ODD domain)-(reporter gene) structure indicates that (HIF-1 binding domain), (mp), (NLS), (ODD domain), and (reporter gene) are connected in this order in the direction of 5'-3'.

7. A transformant obtained by transfecting a host cell with the gene construct according to claim 1.

8. A method for screening a candidate compound or a gene comprising the step of evaluating the candidate compound or the gene that influences expression or activity of a reporter gene in use of the gene construct according to claim 1.

* * * * *

SEQUENCE LISTING

<160> NUMBER OF SEQ ID NOS: 20

<210> SEQ ID NO 1
<211> LENGTH: 2481
<212> TYPE: DNA
<213> ORGANISM: Homo sapiens
<220> FEATURE:
<221> NAME/KEY: CDS
<222> LOCATION: (1)..(2481)

<400> SEQUENCE: 1

```
atg gag ggc gcc ggc ggc gcg aac gac aag aaa aag ata agt tct gaa        48
Met Glu Gly Ala Gly Gly Ala Asn Asp Lys Lys Lys Ile Ser Ser Glu
1               5                   10                  15 cgt cga aaa gaa aag tct cga gat gca gcc aga tct cgg cga agt aaa        96
Arg Arg Lys Glu Lys Ser Arg Asp Ala Ala Arg Ser Arg Arg Ser Lys
            20                  25                  30 gaa tct gaa gtt ttt tat gag ctt gct cat cag ttg cca ctt cca cat       144
Glu Ser Glu Val Phe Tyr Glu Leu Ala His Gln Leu Pro Leu Pro His
        35                  40                  45 aat gtg agt tcg cat ctt gat aag gcc tct gtg atg agg ctt acc atc       192
Asn Val Ser Ser His Leu Asp Lys Ala Ser Val Met Arg Leu Thr Ile
    50                  55                  60 agc tat ttg cgt gtg agg aaa ctt ctg gat gct ggt gat ttg gat att       240
Ser Tyr Leu Arg Val Arg Lys Leu Leu Asp Ala Gly Asp Leu Asp Ile
65                  70                  75                  80 gaa gat gac atg aaa gca cag atg aat tgc ttt tat ttg aaa gcc ttg       288
Glu Asp Asp Met Lys Ala Gln Met Asn Cys Phe Tyr Leu Lys Ala Leu
                85                  90                  95 gat ggt ttt gtt atg gtt ctc aca gat gat ggt gac atg att tac att       336
Asp Gly Phe Val Met Val Leu Thr Asp Asp Gly Asp Met Ile Tyr Ile
            100                 105                 110 tct gat aat gtg aac aaa tac atg gga tta act cag ttt gaa cta act       384
Ser Asp Asn Val Asn Lys Tyr Met Gly Leu Thr Gln Phe Glu Leu Thr
        115                 120                 125 gga cac agt gtg ttt gat ttt act cat cca tgt gac cat gag gaa atg       432
Gly His Ser Val Phe Asp Phe Thr His Pro Cys Asp His Glu Glu Met
    130                 135                 140 aga gaa atg ctt aca cac aga aat ggc ttg gtg aaa aag ggt aaa gaa       480
Arg Glu Met Leu Thr His Arg Asn Gly Leu Val Lys Lys Gly Lys Glu
145                 150                 155                 160 caa aac aca cag cga agc ttt ttt ctc aga atg aag tgt acc cta act       528
Gln Asn Thr Gln Arg Ser Phe Phe Leu Arg Met Lys Cys Thr Leu Thr
                165                 170                 175 agc cga gga aga act atg aac ata aag tct gca aca tgg aag gta ttg       576
Ser Arg Gly Arg Thr Met Asn Ile Lys Ser Ala Thr Trp Lys Val Leu
            180                 185                 190 cac tgc aca ggc cac att cac gta tat gat acc aac agt aac caa cct       624
His Cys Thr Gly His Ile His Val Tyr Asp Thr Asn Ser Asn Gln Pro
        195                 200                 205 cag tgt ggg tat aag aaa cca cct atg acc tgc ttg gtg ctg att tgt       672
Gln Cys Gly Tyr Lys Lys Pro Pro Met Thr Cys Leu Val Leu Ile Cys
    210                 215                 220 gaa ccc att cct cac cca tca aat att gaa att cct tta gat agc aag       720
Glu Pro Ile Pro His Pro Ser Asn Ile Glu Ile Pro Leu Asp Ser Lys
225                 230                 235                 240 act ttc ctc agt cga cac agc ctg gat atg aaa ttt tct tat tgt gat       768
Thr Phe Leu Ser Arg His Ser Leu Asp Met Lys Phe Ser Tyr Cys Asp
                245                 250                 255 gaa aga att acc gaa ttg atg gga tat gag cca gaa gaa ctt tta ggc       816
```

```
                Glu Arg Ile Thr Glu Leu Met Gly Tyr Glu Pro Glu Leu Leu Gly
                            260                 265                 270 cgc tca att tat gaa tat tat cat gct ttg gac tct gat cat ctg acc      864
Arg Ser Ile Tyr Glu Tyr Tyr His Ala Leu Asp Ser Asp His Leu Thr
            275                 280                 285 aaa act cat cat gat atg ttt act aaa gga caa gtc acc aca gga cag      912
Lys Thr His His Asp Met Phe Thr Lys Gly Gln Val Thr Thr Gly Gln
        290                 295                 300 tac agg atg ctt gcc aaa aga ggt gga tat gtc tgg gtt gaa act caa      960
Tyr Arg Met Leu Ala Lys Arg Gly Gly Tyr Val Trp Val Glu Thr Gln
305                 310                 315                 320 gca act gtc ata tat aac acc aag aat tct caa cca cag tgc att gta     1008
Ala Thr Val Ile Tyr Asn Thr Lys Asn Ser Gln Pro Gln Cys Ile Val
                325                 330                 335 tgt gtg aat tac gtt gtg agt ggt att att cag cac gac ttg att ttc     1056
Cys Val Asn Tyr Val Val Ser Gly Ile Ile Gln His Asp Leu Ile Phe
            340                 345                 350 tcc ctt caa caa aca gaa tgt gtc ctt aaa ccg gtt gaa tct tca gat     1104
Ser Leu Gln Gln Thr Glu Cys Val Leu Lys Pro Val Glu Ser Ser Asp
        355                 360                 365 atg aaa atg act cag cta ttc acc aaa gtt gaa tca gaa gat aca agt     1152
Met Lys Met Thr Gln Leu Phe Thr Lys Val Glu Ser Glu Asp Thr Ser
    370                 375                 380 agc ctc ttt gac aaa ctt aag aag gaa cct gat gct tta act ttg ctg     1200
Ser Leu Phe Asp Lys Leu Lys Lys Glu Pro Asp Ala Leu Thr Leu Leu
385                 390                 395                 400 gcc cca gcc gct gga gac aca atc ata tct tta gat ttt ggc agc aac     1248
Ala Pro Ala Ala Gly Asp Thr Ile Ile Ser Leu Asp Phe Gly Ser Asn
                405                 410                 415 gac aca gaa act gat gac cag caa ctt gag gaa gta cca tta tat aat     1296
Asp Thr Glu Thr Asp Asp Gln Gln Leu Glu Glu Val Pro Leu Tyr Asn
            420                 425                 430 gat gta atg ctc ccc tca ccc aac gaa aaa tta cag aat ata aat ttg     1344
Asp Val Met Leu Pro Ser Pro Asn Glu Lys Leu Gln Asn Ile Asn Leu
        435                 440                 445 gca atg tct cca tta ccc acc gct gaa acg cca aag cca ctt cga agt     1392
Ala Met Ser Pro Leu Pro Thr Ala Glu Thr Pro Lys Pro Leu Arg Ser
    450                 455                 460 agt gct gac cct gca ctc aat caa gaa gtt gca tta aaa tta gaa cca     1440
Ser Ala Asp Pro Ala Leu Asn Gln Glu Val Ala Leu Lys Leu Glu Pro
465                 470                 475                 480 aat cca gag tca ctg gaa ctt tct ttt acc atg ccc cag att cag gat     1488
Asn Pro Glu Ser Leu Glu Leu Ser Phe Thr Met Pro Gln Ile Gln Asp
                485                 490                 495 cag aca cct agt cct tcc gat gga agc act aga caa agt tca cct gag     1536
Gln Thr Pro Ser Pro Ser Asp Gly Ser Thr Arg Gln Ser Ser Pro Glu
            500                 505                 510 cct aat agt ccc agt gaa tat tgt ttt tat gtg gat agt gat atg gtc     1584
Pro Asn Ser Pro Ser Glu Tyr Cys Phe Tyr Val Asp Ser Asp Met Val
        515                 520                 525 aat gaa ttc aag ttg gaa ttg gta gaa aaa ctt ttt gct gaa gac aca     1632
Asn Glu Phe Lys Leu Glu Leu Val Glu Lys Leu Phe Ala Glu Asp Thr
    530                 535                 540 gaa gca aag aac cca ttt tct act cag gac aca gat tta gac ttg gag     1680
Glu Ala Lys Asn Pro Phe Ser Thr Gln Asp Thr Asp Leu Asp Leu Glu
545                 550                 555                 560 atg tta gct ccc tat atc cca atg gat gat gac ttc cag tta cgt tcc     1728
Met Leu Ala Pro Tyr Ile Pro Met Asp Asp Asp Phe Gln Leu Arg Ser
                565                 570                 575 ttc gat cag ttg tca cca tta gaa agc agt tcc gca agc cct gaa agc     1776
```

```
Phe Asp Gln Leu Ser Pro Leu Glu Ser Ser Ala Ser Pro Glu Ser
            580                 585                 590 gca agt cct caa agc aca gtt aca gta ttc cag cag act caa ata caa      1824
Ala Ser Pro Gln Ser Thr Val Thr Val Phe Gln Gln Thr Gln Ile Gln
        595                 600                 605 gaa cct act gct aat gcc acc act acc act gcc acc act gat gaa tta      1872
Glu Pro Thr Ala Asn Ala Thr Thr Thr Ala Thr Asp Glu Leu
610                 615                 620 aaa aca gtg aca aaa gac cgt atg gaa gac att aaa ata ttg att gca      1920
Lys Thr Val Thr Lys Asp Arg Met Glu Asp Ile Lys Ile Leu Ile Ala
625                 630                 635                 640 tct cca tct cct acc cac ata cat aaa gaa act act agt gcc aca tca      1968
Ser Pro Ser Pro Thr His Ile His Lys Glu Thr Thr Ser Ala Thr Ser
                645                 650                 655 tca cca tat aga gat act caa agt cgg aca gcc tca cca aac aga gca      2016
Ser Pro Tyr Arg Asp Thr Gln Ser Arg Thr Ala Ser Pro Asn Arg Ala
            660                 665                 670 gga aaa gga gtc ata gaa cag aca gaa aaa tct cat cca aga agc cct      2064
Gly Lys Gly Val Ile Glu Gln Thr Glu Lys Ser His Pro Arg Ser Pro
        675                 680                 685 aac gtg tta tct gtc gct ttg agt caa aga act aca gtt cct gag gaa      2112
Asn Val Leu Ser Val Ala Leu Ser Gln Arg Thr Thr Val Pro Glu Glu
    690                 695                 700 gaa cta aat cca aag ata cta gct ttg cag aat gct cag aga aag cga      2160
Glu Leu Asn Pro Lys Ile Leu Ala Leu Gln Asn Ala Gln Arg Lys Arg
705                 710                 715                 720 aaa atg gaa cat gat ggt tca ctt ttt caa gca gta gga att gga aca      2208
Lys Met Glu His Asp Gly Ser Leu Phe Gln Ala Val Gly Ile Gly Thr
                725                 730                 735 tta tta cag cag cca gac gat cat gca gct act aca tca ctt tct tgg      2256
Leu Leu Gln Gln Pro Asp Asp His Ala Ala Thr Thr Ser Leu Ser Trp
            740                 745                 750 aaa cgt gta aaa gga tgc aaa tct agt gaa cag aat gga atg gag caa      2304
Lys Arg Val Lys Gly Cys Lys Ser Ser Glu Gln Asn Gly Met Glu Gln
        755                 760                 765 aag aca att att tta ata ccc tct gat tta gca tgt aga ctg ctg ggg      2352
Lys Thr Ile Ile Leu Ile Pro Ser Asp Leu Ala Cys Arg Leu Leu Gly
    770                 775                 780 caa tca atg gat gaa agt gga tta cca cag ctg acc agt tat gat tgt      2400
Gln Ser Met Asp Glu Ser Gly Leu Pro Gln Leu Thr Ser Tyr Asp Cys
785                 790                 795                 800 gaa gtt aat gct cct ata caa ggc agc aga aac cta ctg cag ggt gaa      2448
Glu Val Asn Ala Pro Ile Gln Gly Ser Arg Asn Leu Leu Gln Gly Glu
                805                 810                 815 gaa tta ctc aga gct ttg gat caa gtt aac tga                          2481
Glu Leu Leu Arg Ala Leu Asp Gln Val Asn
            820                 825

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
aaccatggcg cctaagaaga agaggaag                                         28

<210> SEQ ID NO 3
<211> LENGTH: 29
<212> TYPE: DNA
<213> ORGANISM: Artificial Sequence
```

```
<220> FEATURE:
<223> OTHER INFORMATION: primer

<400> SEQUENCE: 3
aaccatggtc tgctggaata ctgtaactg                                      29

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
aaggatccac catggaagac gccaaa                                         26

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
ttgatatctt acacggcgat ctttcc                                         26

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
aaagatctgc cccagccgct ggag                                           24

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
aaagatcttt ggcaatgtct ccat                                           24

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
aaagatctcc tagtccttcc gatg                                           24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
aaagatctaa cccattttct actc                                           24
```

```
<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
aaagatctca gttgtcacca tta                                           23

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
aaccatggtc tggaatactg taac                                          24

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
aaccatggta tttatattct gtaa                                          24

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
aaccatggtt gtctgatcct gaatc                                         25

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
aaccatggtc tttgcttctg tgtc                                          24

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
aaccatggtt aatggtgaca actg                                          24

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16
```

```
<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
aaccatggtt gcgctttcag ggcttgc                                          27

<210> SEQ ID NO 18
<211> LENGTH: 27
<212> TYPE: DNA
<213> ORGANISM: Artificial Sequence
<220> FEATURE:
<223> OTHER INFORMATION: primer

<400> SEQUENCE: 18
aaccatggtt gtgctttgag gacttgc                                          27

<210> SEQ ID NO 19
<211> LENGTH: 26
<212> TYPE: DNA
<213> ORGANISM: Artificial Sequence
<220> FEATURE:
<223> OTHER INFORMATION: primer

<400> SEQUENCE: 19
aaagatctca ggacacagat ttagac                                           26

<210> SEQ ID NO 20
<211> LENGTH: 27
<212> TYPE: DNA
<213> ORGANISM: Artificial Sequence
<220> FEATURE:
<223> OTHER INFORMATION: primer

<400> SEQUENCE: 20
aaagatcttt agacttggag atgttag                                          27
```